United States Patent
Walzman

(10) Patent No.: US 12,303,412 B2
(45) Date of Patent: May 20, 2025

(54) ORIENTABLE IMPLANTABLE DEVICE AND METHOD

(71) Applicant: Daniel Ezra Walzman, Teaneck, NJ (US)

(72) Inventor: Daniel Ezra Walzman, Teaneck, NJ (US)

(*) Notice: Subject to any disclaimer, the term of this patent is extended or adjusted under 35 U.S.C. 154(b) by 0 days.

(21) Appl. No.: 18/232,900

(22) Filed: Aug. 11, 2023

(65) Prior Publication Data

US 2025/0049597 A1 Feb. 13, 2025

Related U.S. Application Data

(63) Continuation of application No. 17/515,756, filed on Nov. 1, 2021, which is a continuation-in-part of (Continued)

(51) Int. Cl.
*A61F 2/954* (2013.01)
*A61B 17/00* (2006.01)
(Continued)

(52) U.S. Cl.
CPC ........ *A61F 2/954* (2013.01); *A61B 17/00234* (2013.01); *A61B 17/12113* (2013.01); (Continued)

(58) Field of Classification Search
CPC .............. A61F 2/954; A61F 2/958–2002/9586
See application file for complete search history.

(56) References Cited

U.S. PATENT DOCUMENTS

| | | |
|---|---|---|
| 5,019,090 A | 5/1991 | Pinchuck |
| 5,071,407 A | 12/1991 | Termin et al. |

(Continued)

FOREIGN PATENT DOCUMENTS

| | | | | |
|---|---|---|---|---|
| CN | 105853035 B | * | 11/2018 | ............ A61F 2/90 |
| JP | 2005-506100 | | 3/2005 | |

(Continued)

OTHER PUBLICATIONS

Machine translation of CN10585393B from Espacenet, accessed Sep. 29, 2014, 20 pages. https://worldwide.espacenet.com/patent/search/family/056628724/publication/CN105853035A?q=cn105853035 (Year: 2024).*

(Continued)

*Primary Examiner* — Rebecca S Preston
(74) *Attorney, Agent, or Firm* — Neil D. Gershon

(57) ABSTRACT

An intravascular system having a first catheter having a first non-circular transverse cross-sectional configuration and a first delivery device configured for insertion into the lumen of the catheter. The first delivery device includes an implantable medical device and an elongated member supporting the first medical device such that the first elongated member and the first medical device are movable through the lumen of the first catheter. The first elongated member has a second non-circular transverse cross-sectional configuration corresponding to the first non-circular transverse cross-sectional configuration to thereby inhibit rotation of the first elongated member within the catheter and control orientation of the first medical device relative to the catheter.

17 Claims, 17 Drawing Sheets

Related U.S. Application Data application No. 17/246,853, filed on May 3, 2021, now Pat. No. 11,723,785, and a continuation-in-part of application No. 16/888,813, filed on May 31, 2020, now Pat. No. 11,638,655, said application No. 17/246,853 is a continuation of application No. 16/852,488, filed on Apr. 19, 2020, now Pat. No. 11,045,177.

(60) Provisional application No. 63/109,387, filed on Nov. 4, 2020, provisional application No. 62/921,574, filed on Jun. 25, 2019, provisional application No. 62/921,378, filed on Jun. 12, 2019.

(51) Int. Cl.
| | |
|---|---|
| *A61B 17/12* | (2006.01) |
| *A61F 2/856* | (2013.01) |
| *A61F 2/90* | (2013.01) |
| *A61F 2/95* | (2013.01) |
| *A61F 2/958* | (2013.01) |
| *A61F 2/966* | (2013.01) |
| *A61B 90/00* | (2016.01) |
| *A61F 2/06* | (2013.01) |
| *A61F 2/82* | (2013.01) |
| *A61M 25/00* | (2006.01) |

(52) U.S. Cl.
CPC ........ *A61B 17/12118* (2013.01); *A61F 2/856* (2013.01); *A61F 2/90* (2013.01); *A61F 2/95* (2013.01); *A61F 2/9517* (2020.05); *A61F 2/958* (2013.01); *A61F 2/966* (2013.01); *A61B 2017/00292* (2013.01); *A61B 17/0057* (2013.01); *A61B 2017/1205* (2013.01); *A61B 17/12172* (2013.01); *A61B 2090/3966* (2016.02); *A61F 2002/061* (2013.01); *A61F 2002/823* (2013.01); *A61F 2002/9534* (2013.01); *A61F 2002/9583* (2013.01); *A61F 2230/0004* (2013.01); *A61F 2230/0017* (2013.01); *A61F 2230/0023* (2013.01); *A61F 2250/0023* (2013.01); *A61F 2250/0024* (2013.01); *A61F 2250/0098* (2013.01); *A61M 2025/0008* (2013.01); *A61M 25/0097* (2013.01)

(56) References Cited

U.S. PATENT DOCUMENTS

| | | | |
|---|---|---|---|
| 5,221,261 | A | 6/1993 | Termin et al. |
| 5,306,263 | A | 4/1994 | Voda |
| 5,322,064 | A | 6/1994 | Lundquist |
| 5,534,007 | A | 7/1996 | St. Germain |
| 5,891,057 | A | 4/1999 | Chaisson et al. |
| 6,547,760 | B1 | 4/2003 | Samson et al. |
| 6,723,116 | B2 | 4/2004 | Tahiri |
| 8,465,442 | B2 | 6/2013 | Freed |
| 9,775,730 | B1 | 10/2017 | Walzman |
| 11,045,177 | B2 | 6/2021 | Walzman |
| 11,638,655 | B2 | 5/2023 | Walzman |
| 11,723,785 | B2 | 8/2023 | Walzman |
| 2001/0037141 | A1 | 11/2001 | Yee |
| 2001/0041874 | A1 | 11/2001 | Reydel |
| 2002/0035392 | A1 | 3/2002 | Wilson |
| 2002/0111666 | A1 | 8/2002 | Hart |
| 2002/0121280 | A1 | 9/2002 | Gordon |
| 2002/0143383 | A1 | 10/2002 | Parodi |
| 2003/0139802 | A1 | 7/2003 | Wulfman |
| 2003/0204246 | A1 | 10/2003 | Chu et al. |
| 2003/0225365 | A1 | 12/2003 | Greff et al. |
| 2005/0049607 | A1 | 3/2005 | Hart et al. |
| 2005/0049609 | A1 | 3/2005 | Gunderson |
| 2005/0222666 | A1* | 10/2005 | Lualdi ............... A61F 2/958 |
| | | | 606/108 |
| 2005/0228359 | A1 | 10/2005 | Doyle |
| 2006/0149127 | A1 | 7/2006 | Seddiqui |
| 2006/0229657 | A1 | 10/2006 | Wasicek et al. |
| 2006/0271162 | A1 | 11/2006 | Vito et al. |
| 2007/0055340 | A1 | 3/2007 | Pryor |
| 2007/0060911 | A1 | 3/2007 | Webster et al. |
| 2007/0219619 | A1 | 9/2007 | Dieck et al. |
| 2007/0270935 | A1 | 11/2007 | Newhauser |
| 2007/0282419 | A1 | 12/2007 | Hilaire |
| 2008/0015674 | A1 | 1/2008 | Austin |
| 2008/0172122 | A1 | 7/2008 | Mayberry et al. |
| 2008/0281394 | A1 | 11/2008 | Jones |
| 2009/0192584 | A1 | 7/2009 | Gerdts |
| 2011/0118841 | A1 | 5/2011 | Reiley |
| 2011/0295364 | A1 | 12/2011 | Konstantino |
| 2012/0071987 | A1 | 3/2012 | Levy |
| 2012/0130192 | A1 | 5/2012 | Rasmussen |
| 2012/0290067 | A1 | 11/2012 | Cam |
| 2012/0316632 | A1 | 12/2012 | Gao |
| 2013/0338752 | A1 | 12/2013 | Geusen et al. |
| 2014/0025151 | A1 | 1/2014 | Gao |
| 2014/0031788 | A1 | 1/2014 | Sung et al. |
| 2014/0277397 | A1 | 9/2014 | Lorenzo |
| 2014/0288631 | A1 | 9/2014 | Falotico et al. |
| 2015/0094759 | A1 | 4/2015 | Wolinsky et al. |
| 2017/0239046 | A1 | 8/2017 | Essinger et al. |
| 2017/0281915 | A1 | 10/2017 | Jalgaonkar |
| 2018/0153690 | A1 | 6/2018 | Spence |
| 2018/0236205 | A1 | 8/2018 | Krautkremer |
| 2018/0243113 | A1 | 8/2018 | Walzman |
| 2018/0289884 | A1 | 10/2018 | Criado et al. |
| 2019/0151072 | A1 | 5/2019 | Walzman |
| 2020/0253766 | A1 | 8/2020 | Walzman |

FOREIGN PATENT DOCUMENTS

| | | |
|---|---|---|
| JP | 2008-502378 | 1/2008 |
| JP | 2010-515553 | 5/2010 |
| JP | 2012-029980 | 2/2012 |
| WO | WO 2005/112823 | 12/2005 |
| WO | WO 2018/073830 | 4/2018 |
| WO | WO 2020/251777 | 12/2020 |
| WO | WO 2020/251788 | 12/2020 |

OTHER PUBLICATIONS

JA Office Action JP2021-574225 Dated: Jan. 23, 2024.
JA Search Report JP2021-574225 Dated: Jan. 19, 2024.
European Search Report EP 20 82 3441 (06.27.2023).
PCT/US2020/035489 International Search Report and Written Opinion (Sep. 8, 2020).
PCT/US2020/035017 International Search Report and Written Opinion (Oct. 6, 2020).
PCT/US2021/057506 International Search Report and Written Opinion (Mar. 25, 2022).

* cited by examiner

   
FIG. 7A   FIG. 7B   FIG. 7C   FIG. 7D
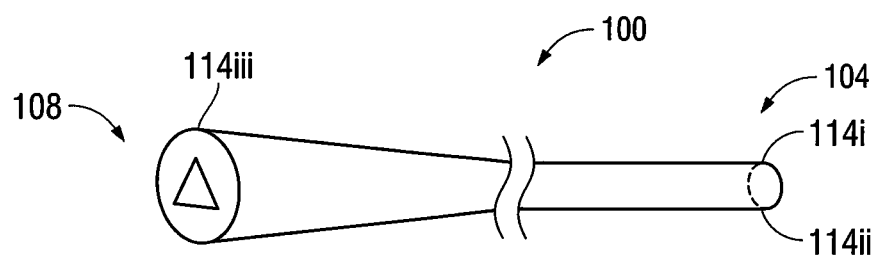
FIG. 7E
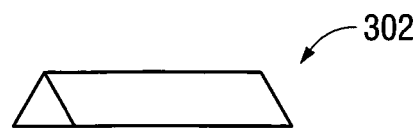
FIG. 8
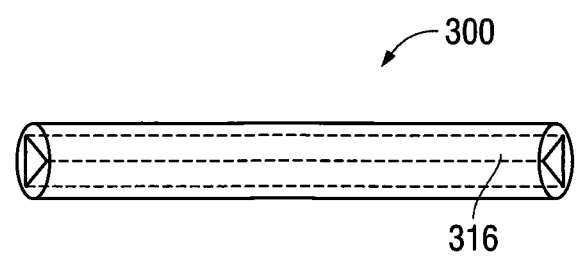
FIG. 9

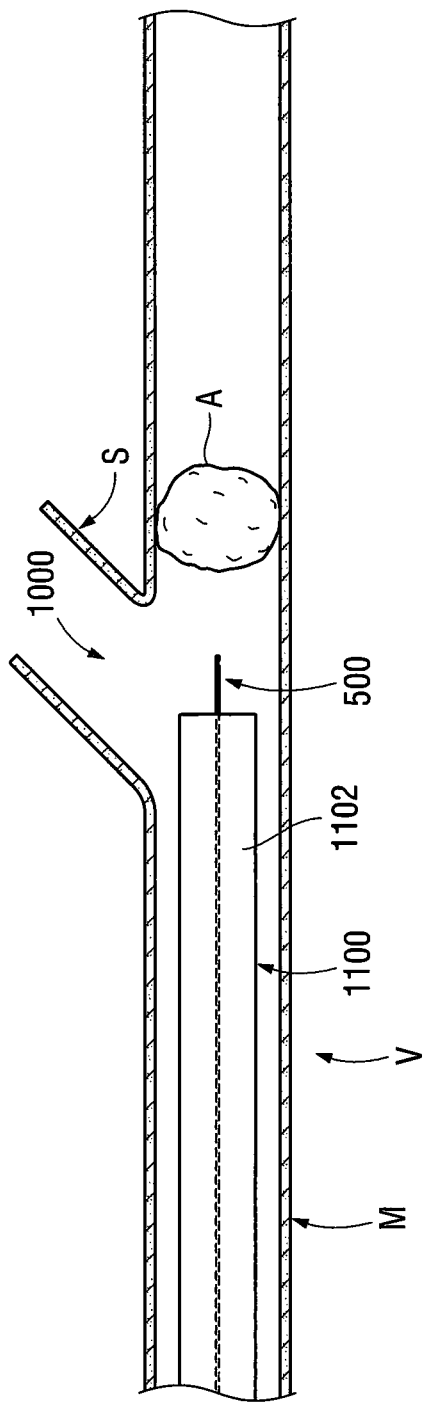
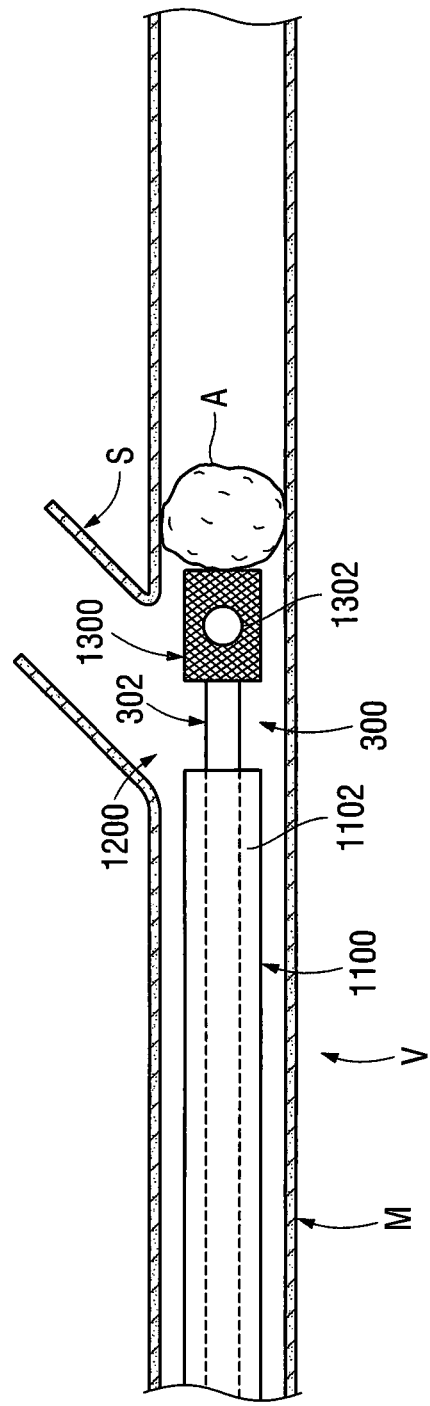

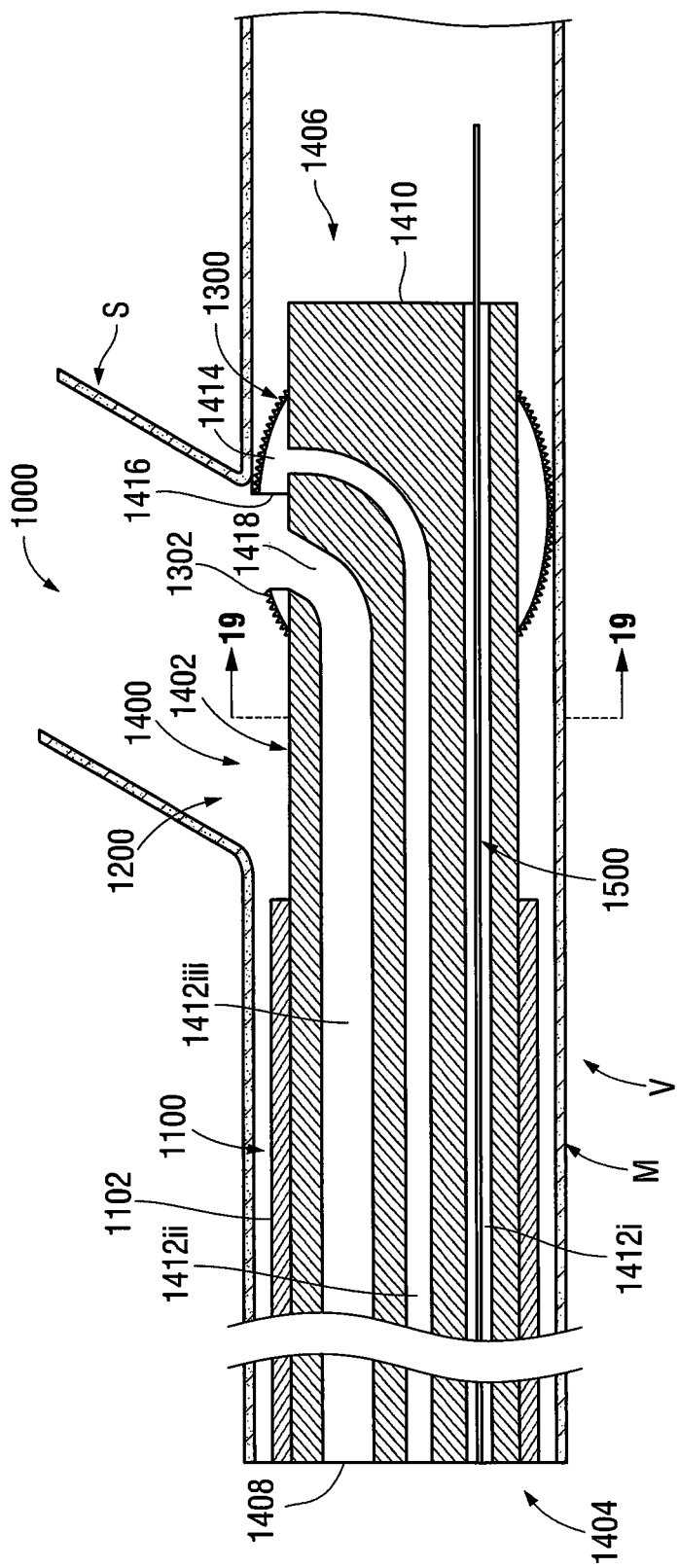
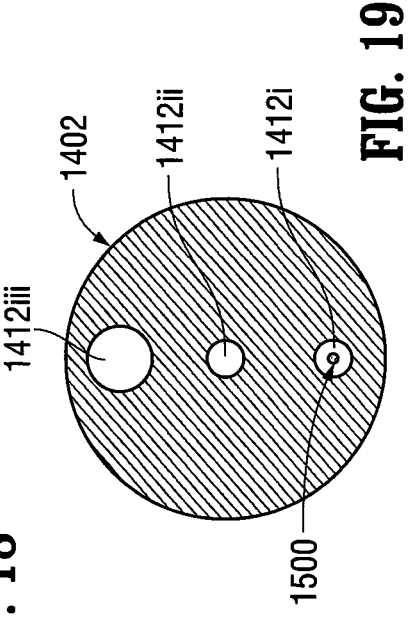
FIG. 18
FIG. 19

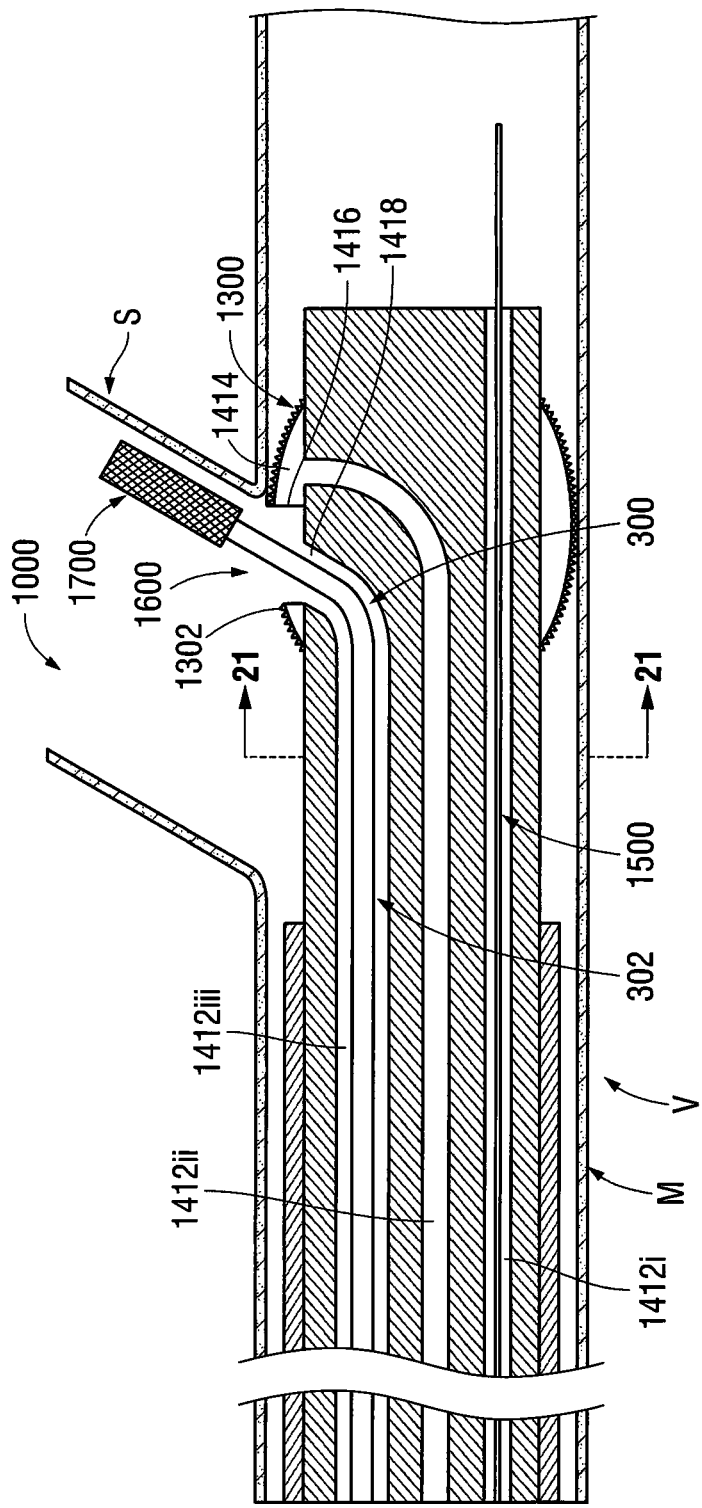
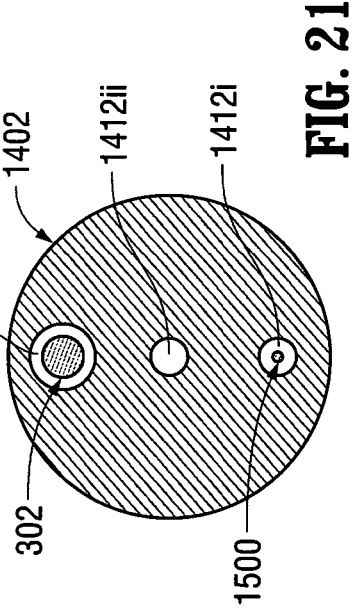
FIG. 20
FIG. 21

ORIENTABLE IMPLANTABLE DEVICE AND METHOD

CROSS-REFERENCE TO RELATED APPLICATION(S)

This application is a continuation of U.S. application Ser. No. 17/515,756, filed on Nov. 1, 2021, which claims priority to provisional application 63/109,387, filed on Nov. 4, 2020, and is a continuation-in-part of U.S. application Ser. No. 16/888,813, filed on May 31, 2020, now U.S. Pat. No. 11,638,655, which claims priority to provisional application 62/921,574, filed on Jun. 25, 2019, and is a continuation-in-part of U.S. application Ser. No. 17/246,853, filed May 3, 2021, which is a continuation of U.S. application Ser. No. 16/852,488, filed on Apr. 19, 2020, now U.S. Pat. No. 11,045,177, which claims priority to 62/921,378, filed Jun. 12, 2019. The entire contents of each of these applications are incorporated herein by reference.

BACKGROUND OF THE INVENTION

Field of the Invention

The present disclosure relates to medical devices used to treat vascular pathologies (e.g., aneurysms, fistulas, ruptures, narrowings etc.) in intracranial or other tortuous blood vessels (vasculature). In one particular aspect, for example, the present disclosure relates to endovascular devices that are configured to deploy a stent and/or other devices (e.g., a flow-diverting stent, a covered stent, a caped stent, a fenestrated stent, a branched stent, a variable porosity stent, etc.) in a desired orientation to treat such vascular pathologies.

Prior Art

The prior art teaches the use of a number of devices to treat vascular pathologies. One such device is a differentially porous (variable porosity) stent that includes asymmetrical braiding or coils so as to create areas of lesser or greater blood flow as may be desired. Fenestrated and branched devices have been effectively employed in the aorta and its immediate branches, and other applications having larger blood vessels with little tortuosity. Although the prior art has disclosed the theoretical application of such devices intracranially and in other tortuous and distal vasculature, no device or method has been described that can reliably deploy such devices in their desired (rotational) orientation. This is similarly true for other vascular devices that could more ideally be customized to a particular anatomy if they were able to be positioned reliably in a desired orientation. The constraints of intracranial or other tortuous vasculature have to date precluded the use thereof in these areas.

U.S. Pat. No. 9,775,730 (Walzman) teaches a covered stent device capable of safe and effective delivery and deployment into tortuous vessels to effectively divert blood flow away from the vascular abnormality while allowing blood to flow to healthy tissue distal to the targeted treatment area and still resulting in blood stasis and thrombus formation inside the aneurysm, fistula, etc.

U.S. Pat. Publ. No. 2019/0151072 A1 (Walzman) teaches a caped stent providing a cover having a single attachment point and a free end that can be overlapped, thereby providing better conformity to target vessels than existing covered stents.

U.S. Pat. No. 8,398,701 B2 (Berez et al.) teaches a vascular occluding device deployable on a microcatheter. The occluding device includes an asymmetrical braid or differential lattice densities, as well as and corresponding/opposite variable densities of porosity to modify blood flow in a vessel while maintaining flow to surrounding tissue. Berez teaches that the flexibility of the device particularly suits it for treating aneurysms in the brain. Berez describes an embodiment including less coverage on one side at the same segment along the length of the cylinder versus the other side. For example, the area having less porosity (i.e., more coverage) should be positioned to cover an aneurysm for stagnation of flow in the aneurysm and subsequent thrombosis. The other side of the device having more porosity should be positioned on one side of a vessel or covering a branch to allow continuation of adequate flow and to prevent obstruction of flow to the branch and its distal tissue. However, Berez and others have not devised a way to consistently and reliably deploy such devices in the optimal desired radial orientation, and no such devices are available.

In the extreme, an endovascular device may provide additional porosity by including a fenestration, allowing no obstruction whatsoever of blood flow to the origin of a branch vessel. This may be combined with a full cover at or near an opposing side to cut blood flow to a target aneurysm or fistula altogether.

A common blood vessel difficulty is the persistent blood flow in the aneurysm sac extrinsic to an endograft. In fact, this is the most common complication after endovascular aneurysm repair (EVAR) with stent grafts. Such endoleaks are ameliorated by a number of means. For example, Walzman's utility application Ser. Nos. 15/732,147 and 15/732,365 teach the use of hydrogel to prevent endoleaks.

The prior art also teaches endovascular coiling as a minimally invasive technique performed to prevent blood from flowing into some saccular aneurysms. This treatment results in the coil inducing embolization (clotting) of the aneurysm, which prevents blood from flowing into the aneurysm, which in turn, prevents rupture and subsequent subarachnoid hemorrhage. Endovascular coiling however may result in procedural complications include thromboembolism, cerebral embolization, aneurysm perforation, parent artery occlusion, coil migration, arterial dissection, and others. The prior art also teaches stent-assisted coiling. The stent-assisted coiling also has some of the same short comings related to stent placement and placing a stent in the parent artery requires prolonged use of anti-platelet agents to reduce the risk of thrombosis-based stenosis within the stent.

Some aneurysms and fistulas are ideally treated with covered stents, which can most directly cover the hole of the fistula or the neck of the aneurysm and reconstruct the vessel wall, immediately redirecting blood flow into the normal path of the parent vessel. However, there is no covered neuro-stent currently available in the United States. The U.S. Food and Drug Administration (FDA) has examined and tested such covered neuro-stents but none has "FDA approval," which means that the FDA has not decided the benefits over the existing treatment options outweigh the potential risks for the item's planned use. Additionally, there are currently no covered stents that are effective in severely tortuous anatomy in other parts of the body, including but not limited to splenic artery aneurysms and pulmonary arteriovenous fistulas.

A potentially significant use of covered neuro-stents is for the treatment of fistulas, particularly for Carotid cavernous fistula (CCF) which is an abnormal communication between the cavernous sinus and the carotid arterial system.

Other treatment of aneurysms includes surgical clipping of an intracranial aneurysm, which involves the application of a clip across the neck of the aneurysm. This treatment has several shortcomings including that it requires an open operation and physical manipulation of the brain. Sometimes surgical bypass is considered as well, but typically is associated with even higher rates of morbidity and mortality.

Additionally, prior art teaches the use of flow diversion devices to divert flow away from the aneurysm by placing a mesh stent or a structure similar to a stent, on the aneurysm neck along the parent artery. The use of these devices allows for thrombus formation inside the aneurysm. However, increased technical complications can develop following the deployment of flow diverters.

Additionally, because they do not completely block flow, they are not effective in the treatment of fistulas and ruptured vessel. Similarly, there is currently no effective vessel-sparing treatment of an iatrogenic rupture of an intracranial artery. Current treatment requires closing the ruptured artery with coils and/or liquid embolics to stop the bleeding, usually with significant resulting morbidity from ischemic injury to that arterial territory. Furthermore, when treating aneurysms with these devices, the aneurysm thromboses over time, a lag period, and is not immediately cured. This leaves the patient at risk of aneurysmal rupture during lag period. This can be especially problematic when treating ruptured aneurysms, which have high short-term re-rupture rates. Still further, when using current flow-diverting stents, many branch vessels are often crossed with the device, often resulting in narrowing's developing at the origins of these branches and sometimes resulting in occlusions and/or injury as well.

Additionally, there are devices to treat vascular outpouchings with intrasaccular, occlusive devices, including for example the W.E.B. (Terumo/Microvention) and Watchman (Boston Scientific). However, current technologies use limited sizes and shapes of these devices.

More customized devices that can potentially conform better to the anatomy of a particular outpouching are difficult to orient properly utilizing current technologies. The need exists to ameliorate these difficulties and to provide accurate rotational intravascular positioning of devices including fully or partially customized intraocular devices, variable porosity stents, covered and partially covered devices, etc., via endovascular delivery and n tortuous vascular anatomies.

A need exists for an endovascular device capable of endovascular intervention for immediate cure of select intravascular aneurysm or fistula, while ameliorating the difficulties and shortcomings associated with the currently available technologies. More particularly, a need exists for a covered stent which allow said stent freedom of motion and bending without kinking around tight bends in tortuous anatomy.

Most covered stents involve producing a cylinder of a stent "skeleton" or "frame" out of semi rigid materials such as metal alloys, and then attaching an impermeable "cover" to said frame. The prior art teaches such attachments are diffuse and located throughout the covering of a stent, along fixed intervals of said covering and frame, and consequently significantly limit flexibility of the device.

All currently available flow-diverting stents have relatively uniform patterns of coverage and porosity throughout. No reliable means has been developed to successfully deploy a device that has differential porosity along different circumferentially radial segments.

For neuro-endovascular procedures (and other tortuous vascular anatomies), there is no known device or method allows for precise positioning of such a differentially porous device to achieve an ideal ratio of covering and porosity where desired, and allowing flow where desired. Unlike larger vasculature (e.g., aortic), devices deployed through intracranial or other tortuous, circulatory anatomy are not susceptible to manual rotation at the hub end having an effect to rotate the intracranial end.

Thus, there is a need for a device that can be reproducibly positioned/landed in the appropriate orientation, such that area of dense coverage and corresponding low porosity (or complete impermeability in an extreme case, or a fenestration in another extreme case) is deployed on the desired side, while the low density of coverage and corresponding high porosity (and/or fenestration with no coverage at all in an extreme case) is deployed on the desired side. Additionally, there is a need for branched covered and flow diverting devices in distal and tortuous vasculatures. Currently such devices are not available for use in neuro-endovascular procedures, and are similarly not available in other tortuous vascular anatomies, because devices, systems, and methods to deploy such devices consistently and accurately in the desired orientation do not exist.

Similarly, in cardiac, peripheral and other vasculatures, there is a need for more effective bifurcated stent constructs to minimize the obstruction of side branches during various stenting procedures. The systems and methods described herein facilitate accurate positioning of fenestrations in a multiple stent construct to minimize the risk of obstructing branches while also facilitating more effective placement of stents across bifurcations. These constructs can effectively treat atherosclerotic narrowing's, aneurysmal diseases, dissections, fistulas, and other pathologies.

Therefore, were one to deploy such a device the ultimate orientation upon positioning would be random. For example, with the case just described, the exact opposite from ideal could occur. That is, the fenestration might end up over the aneurysm, thereby increasing flow to the lesion; while the area of high-density coverage might end up over the origin of a normal branch vessel, causing a lack of flow to said branch, and subsequent ischemic injury. The device can work easily in straight anatomy of short distances, where a catheter can easily and accurately be rotated along its entire length from its proximal hub.

Again, using the extreme example of a fenestrated device, branched devices could also be built in vivo, by deploying a fenestrated device with the fenestration over the origin of a branch, and the deploying another device from the fenestration, and into the branch. The second device can be slightly larger in diameter proximally, at the fenestration, to ensure slight overlap, without covering the primary distal branch/vessel. Similarly, a device could be built that includes multiple branches, through multiple fenestrations, provided all fenestrations are in proper relative distance and orientation to the native branches.

This concept was described elegantly by Ruiz in U.S. Pat. No. 6,261,273 B1 for an Access System for Branched Vessels [and] Methods of Use. However, Ruiz discloses the building of a directional sheath or catheter in vivo, rather than an implant. Like the Berez device, however, the Ruiz device can work easily in straight anatomy of short distances, where a catheter can easily and accurately be rotated along its entire length from its proximal hub.

Rotation is not effective with current technologies for positioning in tortuous and/or longer vascular anatomies, in which catheters do not respond in a similarly predictable fashion. This presents a difficulty when a stent device, which is usually crimped for delivery, is advanced into a delivery catheter, typically using a delivery wire and/or hypotube, in a particular arrangement. The stent will exit the delivery catheter in an unpredictable arrangement or orientation.

Furthermore, "Y" shaped stents were not heretofore practical to deploy or assemble at branches in cranial or other tortuous vascular anatomy. There exists a need for Y, bifurcated, and otherwise branched stent devices that may be effectively deployed or assembled in such anatomy. Additionally, in order to safely deploy such branches without safely and accurately, and overlapping the fenestration only slightly consistently, novel devices and methods are needed to more precisely land the proximal end of such stent devices.

Thus, a need exists for a covered or partially covered neuro stent capable of use intracranially or in other tortuous anatomy outside of the brain, which device's more porous and less porous areas may be positioned as desired with respect to one or more branch vessels and at least one aneurysm or fistula, respectively. Additionally, there is a need for similar covered or partially covered branched devices as well. The present disclosure satisfies these unmet needs.

A need also exists for fenestrated and variable coverage and variable porosity stents, wherein the fenestrations and regions of decreased porosity along the circumference of a device can be accurately positioned, in any anatomy. This can be used in vascular applications as well as both vascular and nonvascular endoscopic applications.

SUMMARY OF THE INVENTION

Disclosed herein are methods and devices that facilitate the correct orientation of an occlusion device (e.g., in an intracranial context), such as a stent having differential porosity, with respect to desired areas of greater or lesser blood flow (e.g., branch vessels and aneurysms, respectively). For example, in certain embodiments, the devices and methods described herein may be particularly adapted for use in treating aneurysms and other vascular outpouchings and fistulas in intracranial or other tortuous vasculature, as well as vascular narrowing and other pathologies.

The methods and devices described herein may be used for treatments that require the precise orientation of a device (e.g., a stent, an intrasaccular device, etc.) within the vasculature and/or other luminal structures, which may require travel through long and twisted blood vessels prior to reaching the target area. For example, it is envisioned that the methods and devices described herein may be used in connection with the orientation of asymmetric discs in aneurysm necks or stents in GI/biliary tract (e.g., vascular, endoscopic, etc.).

Known devices and methods are difficult to properly orient due to several factors, particularly in the context of tortuous vasculature. For example, the (working) lumens of known delivery catheters (through which stents may be deployed) are typically tubular with circular (round) (transverse) cross-sectional configurations, as are the outer diameter/surface of the wires over which most balloon-mounted stents are delivered and the inner diameter/surface of known delivery balloon catheters. As a result, stents will generally be caused to rotate during deployment in an unpredictable fashion. Additionally, as catheters are advanced through tortuous anatomy, the catheters themselves can rotate (twist), and do so in an unpredictable fashion. Achieving the desired radial placement can therefore be cumbersome and can result in extending procedure times, improper placement, and other negative consequences. The methods and devices described herein address this shortcoming.

Differentially porous (variable porosity) stents (or other such braided-, mesh-, or weave-type therapeutic devices) may be oriented to a degree of desired flow or blockage. Some stents described by Walzman (Ser. No. 11/007,048—"caped stent") optionally having a free-floating cover that is designed to optimize insertion into tortuous anatomy. Among its unique structural elements are a single circumferential attachment point at one end (as small as 1 nm), overlapping circumferential shingles and overlapping geometric shingles. Some embodiments can have fenestrations of the covering as well. Other stents are disclosed in Walzman U.S. Pat. No. 9,775,730. The entire contents of both of these Walzman patents are incorporated herein by reference.

The stent can have one or more fenestrations. In some embodiments, the stent can have a porosity of less than 28%; in other embodiments, the stent can have a porosity of greater than 28%. In some embodiments, the stent has a variable porosity in different regions along a length and/or along a circumference.

The devices described herein may optionally be deployed under flow arrest (e.g., via pharmacologic means or via delivery through a balloon guide catheter with temporary balloon inflation or other means) to minimize the possibility of blood flow affecting positioning as it is unsheathed.

In other embodiments, it is envisioned that the aforementioned covering may not fully enclose (encircle) a given segment of the stent, thus allowing for variable porosity along the circumference of the stent (e.g., the stent may include a first (covered) circumferential area with decreased porosity relative to a second (uncover) circumferential area). Varying the porosity of the stent facilitates the preservation of the origin of a branch vessel that might arise from the parent vessel along the same segment of the pathology in the parent vessel pathology (e.g., opposite to a fistula or the neck of an aneurysm). The devices and methods described herein allow for more accurate positioning (landing) of stents. For example, if a fenestration in a first stent is placed over the origin of a branch utilizing the devices and methods described herein, the devices and methods described herein can further facilitate the accurate placement of a second stent such that the second stent can be landed in a precise location so as to only overlap the first stent in a desired area (e.g., around the fenestration) and thereby reduce (if not completely eliminate) leaks between the two stents while avoiding unwanted obstruction of the primary vessel by the second stent.

The present disclosure also describes in some embodiments inner "unsheathing" hypotube or wire, which may include a reverse cone (e.g., wings) at a distal end thereof that are configured to cover a stent in the proximal direction. The stent can be mounted on the distal end of an outer hypotube. The inner hypotube goes through the outer hypotube, with its wings extending back over the distal end of the outer hypotube, and over the stent mounted thereon, and constrains the stent, which is often self-expanding in this variant. Once the stent is in the desired position, the outer hypotube can be held in place, while the inner hypotube is advanced. As the inner hypotube is advanced, its back wings are also advanced, and releases its constraint from the stent in a proximal to distal fashion. Thereby, the proximal stent is released from its constraint first, and expands for deployment. If the proximal portion position of landing is not optimal, it can be re-sheathed by pulling the inner hypotube back again. The stent can then be repositioned, and deployment can resume.

The present disclosure describes catheters and wires that include non-circular transverse cross-sectional configurations (e.g., shapes) of inner catheter lumens and/or outer diameters which facilitate mating engagement with each other. Depending on the particular device and procedure, the catheter may be deployed first, and a stent or other device may be delivered therethrough over a corresponding shaped wire; wherein the wire shape correlates with the inner diameter of the stent delivery catheter. In some configurations the wire is delivered first to the lesion site, and a stent mounted catheter is then delivered over it. It is envisioned that any such systems may be adapted for "rapid-exchange" or "over-the-wire" delivery. In other configurations, a catheter with a particular non-circular inner diameter circumferential shape can first be delivered to a lesion site over any wire. The initial wire is then removed and then a stent (or other device) mounted on a corresponding-shaped outer-diameter wire is delivered through said catheter and to the lesion site. It is envisioned that the former configuration may be more common with balloon-mounted stents and that the latter configuration is more common with self-expanding stents. It should be appreciated, however, that the former configuration may also be applied to self-expanding stents and that the latter configuration may be applied to balloon-mounted stents. Furthermore, when a wire with a non-circular outer shape is placed first, it may optionally have a stability component at or near its distal end, which would stabilize the rotational orientation of the wire and prevent its rotation during device delivery.

As elaborated upon below, the interfaces between the devices facilitated by the aforementioned non-circular transverse cross-sectional configurations (e.g., the engagement between a wire and a catheter) inhibit (if not entirely prevent) relative rotation between the devices while allowing for relative axial (longitudinal) movement (e.g., sliding), even in those embodiments in which a stent may be located between the devices (e.g., over a portion of the wire). The devices described herein thus provide for adequate freedom of movement to permit the delivery of a catheter over a wire, or the delivery of a wire through a catheter, without undo force.

In some versions (e.g., in the context of branched stenting), a wire can be placed in each of first and second branches. The wire in the first branch may then be placed through a distal end hole of the delivery catheter and the catheter may be oriented such that a side-hole in the catheter is positioned at (or adjacent to) a stent side fenestration. The wire in the second branch can then be backloaded into the side-hole (e.g., to facilitate proper positioning of the side-hole relative to the origin of the side branch while maintaining wire access to the side branch).

It is also envisioned that positioning of the initial wire or catheter can dictate the manner in which a subsequent stent or wire is delivered based upon an observed degree of rotation from the back of the wire or the hub of the catheter. For example, rotation of a "12 o'clock marker" on the back of the wire or the hub of the catheter may be observed (measured) relative to the corresponding "12 o'clock marker" on the catheter near its distal end at the lesion site. In these versions, a dual-lumen delivery catheter may optionally be employed to deploy (deliver) one or more stents. Such dual-lumen primary delivery catheters include a (first) primary lumen that extends between a proximal end hole and a distal end hole and a (second) secondary lumen that extends between the proximal end hole and a side-hole, which is positioned at (or adjacent to) a fenestration in a primary (first) stent. Via use of the delivery catheter, the primary stent, which may be mounted on a balloon on the primary catheter, can be positioned (deployed) across a lesion in one branch (e.g., a main branch) of the blood vessel (in any necessary or desired orientation) relative to a side branch of the blood vessel. A secondary wire can then be delivered through the secondary lumen and the side-hole and a corresponding hole in the balloon and first stent, into the side branch prior to deployment of the primary stent. Following deployment of the primary stent, the primary delivery catheter can be withdrawn, leaving the secondary wire in place within the side branch of the blood vessel. A secondary stent can then be delivered (e.g., using an additional delivery catheter) and deployed either in the side branch exclusively or such that the secondary stent spans the main branch and the side branch (e.g., such that a first section or portion of the secondary stent is positioned within the main branch and a second section or portion of the secondary stent is positioned in the side branch). In certain embodiments and procedures, it is envisioned that secondary stent may be positioned so as to overlap the primary stent. For example, it is envisioned that the secondary stent may be configured and positioned to overlap (overlie) a proximal portion of the primary stent. The secondary stent may also optionally have a fenestration where it crosses the primary branch. Both "over-the-wire" and "rapid exchange" devices, and combinations thereof, are envisioned within the scope of the present invention. With rapid exchange catheters, the proximal hole for the wire insertion is spaced distally from the proximalmost end of the catheter.

In one aspect of the present disclosure, an intravascular device is disclosed that includes a primary (first) wire (e.g., a guide wire), a delivery catheter, and a primary (first) stent that is loaded onto (e.g., supported by) the delivery catheter. The primary wire includes a fixed, non-circular transverse cross-sectional configuration (e.g., a non-circular outer (circumferential) contour (surface, shape)) over a majority of its length. The primary wire also includes a (first) marker (e.g., a radiopaque marker) at or adjacent to a proximal end thereof and a (second) marker (e.g., a radiopaque marker) at or adjacent to a distal end thereof. The markers can be located in identical circumferential (rotational) positions along an outer surface of the primary wire. In one particular embodiment, for example, the markers are each located in a "twelve o'clock" position.

The delivery catheter includes a proximal end, a distal end, and an inner primary lumen that defines a fixed, non-circular transverse cross-sectional configuration (e.g., a non-circular inner contour (surface, shape)) that corresponds to the transverse cross-sectional configuration defined by the primary wire. The outer diameter of the catheter may be round or any other shape. The delivery catheter optionally includes an "over-the-wire" configuration and slidably receives the primary wire such that the delivery catheter is (at least partially) positioned about the primary wire. Due to the corresponding non-circular transverse cross-sectional configurations defined by the primary wire and the inner lumen of the delivery catheter, the primary wire is insertable into the delivery catheter in a plurality of discrete (rotational) orientations, the number of which is determined by the particular configurations of the primary wire and the delivery catheter. For example, in one particular embodiment, the primary wire and the delivery catheter may include corresponding triangular transverse cross-sectional configurations, which facilitate insertion of the primary wire into the delivery catheter in three distinct (rotational) orientations that are offset from each other by (approximately) 120°. The non-circular transverse cross-sectional configurations of the primary wire and the delivery catheter allow the relative (rotational) orientations of the primary wire and the delivery catheter to be maintained during advancement of the delivery catheter through the blood vessel.

The delivery catheter may include a (third) marker (e.g., a radiopaque marker) at or adjacent to the distal end thereof. The delivery catheter is configured for insertion into and movement through a blood vessel to a target lesion, to stop at a location proximal to the target lesion, to deliver the primary stent, and for withdrawal from the blood vessel.

During use, the delivery catheter is rotated into a predetermined orientation prior to insertion of the primary wire, which results in corresponding rotation of the primary stent, when the stent is mounted on the primary catheter, such as over a balloon mounted on the primary catheter, to allow for advancement of the delivery catheter and the primary stent into the blood vessel, and deployment of the primary stent, in a predetermined (rotational) orientation.

In certain embodiments, the delivery catheter may further include at least one inflatable member, e.g., a balloon, and at least one secondary lumen that is (solely) configured to support inflation and deflation of the at least one balloon.

In certain embodiments, the primary stent may be loaded onto the at least one balloon.

In certain embodiments, the stent may include a differentially porous configuration. For example, the primary stent may include a first region including a first porosity (e.g., a covered area) and a second region including a second, different porosity (e.g., an uncovered area).

In certain embodiments, the primary stent may include at least one fenestration.

In certain embodiments, the primary stent may include at least one region that is substantially impermeable to fluid.

In certain embodiments, the intravascular device may further include at least one adhered compound (e.g., on the primary stent, and/or on other components).

In certain embodiments, the primary stent may include at least one radiopaque marker.

In certain embodiments, the at least one balloon may include at least one radiopaque marker.

In certain embodiments, the primary stent may include at least one radiopaque marker.

In certain embodiments, the primary stent may be configured (e.g., optimized) to facilitate the treatment of a narrowed lumen of the blood vessel.

In certain embodiments, the intravascular device may include a lubricious surface coating.

In certain embodiments, the delivery catheter may include a configuration supporting rapid-exchange.

In certain embodiments, the delivery catheter may include a configuration supporting over the wire insertion with a proximal end hole at the proximalmost end of the catheter.

In certain embodiments, the primary wire may include at least one anchor at or adjacent to the distal end thereof.

In certain embodiments, the at least one anchor may include a tortuous (e.g., a spring-like) configuration.

In certain embodiments, the at least one anchor may include a branched wire segment. For example, the branched wire segment may split into at least two segments such that, upon the application of a predetermined radial force or other detachment mechanism, the at least two segments are directed into walls of the blood vessel in different directions.

In certain embodiments, the at least one anchor may be configured such that the branched wire segment is moved from a first (insertion, inactive, collapsed) configuration, in which the at least two segments are positioned in generally adjacent relation, into a second (anchoring, active, expanded) configuration, in which the at least two segments are separated from each other to thereby anchor the primary wire within the blood vessel upon the application of an external stimulus.

It is envisioned that the at least one anchor may be moved from the first configuration into the second configuration upon the application of any suitable stimulus including, for example, a thermal stimulus, an electric stimulus, a mechanical stimulus, a magnetic stimulus, a hydrostatic stimulus, etc.

In certain embodiments, the at least one anchor may include a balled wire.

In certain embodiments, the at least one anchor may include a retrievable stent.

In certain embodiments, it is envisioned that the primary wire and the at least one anchor may be delivered through a secondary catheter.

In certain embodiments, the secondary catheter may be inserted over a secondary wire.

In certain embodiments, the intravascular device may include an IVUS catheter with an inner lumen that defines a fixed, non-circular transverse cross-sectional configuration (e.g., a non-circular inner contour (surface, shape)) that corresponds to the inner lumen of the primary catheter and the transverse cross-sectional configuration defined by the primary wire, whereby the IVUS catheter may be advanced over the primary wire and subsequently removed before insertion of the delivery catheter (e.g., to optimize imaging and orientation of the target lesion, side branch (branches) of the blood vessel, etc.).

In certain embodiments, the IVUS catheter may include a (fourth) marker (e.g., a radiopaque marker) that is positioned in correspondence with the (third) marker on the delivery catheter (e.g., in the "twelve o'clock" position).

In certain embodiments, the delivery catheter may include a tertiary lumen.

In certain embodiments, the tertiary lumen and/or other lumen may include a "peel-away" (side) slit up to a rapid exchange length lumen.

In certain embodiments, the tertiary lumen may be configured to receive and deliver a tertiary wire (e.g., into a side branch of the blood vessel).

In certain embodiments, the tertiary lumen may terminate in a side-hole that is located proximally of a distal end hole defined by the inner lumen such that the tertiary wire is deliverable into the blood vessel through the side-hole.

In certain embodiments, the at least one balloon may include a fenestration.

In certain embodiments, the at least one balloon may be configured such that the fenestration is generally aligned with (e.g., overlaps or overlies) the side-hole defined by the tertiary lumen.

In certain embodiments, the primary stent may include a fenestration and may be loaded onto the at least one balloon such that the fenestration of the primary stent is generally aligned with (e.g., overlaps or overlies) the fenestration of the at least one balloon and the side-hole.

In certain embodiments, the tertiary wire may include a distal anchor.

In certain embodiments, the tertiary wire may include a fixed, non-circular transverse cross-sectional configuration (e.g., a non-circular outer (circumferential) contour (surface, shape)) over a majority of its length.

In certain embodiments, a secondary delivery catheter may be employed to deliver a secondary stent. In such embodiments, the secondary delivery catheter may include at least one balloon.

In certain embodiments, the secondary stent may be mounted on the at least one balloon of the secondary delivery catheter.

In certain embodiments, the secondary stent may include at least one fenestration. For example, the secondary stent may include an annular (e.g., round, circular, oval, etc.) opening (hole) that is configured to overlap an ostium (origin) of a vessel branch.

In certain embodiments, the secondary stent may include at least one secondary compound adhered thereto.

In certain embodiments, the secondary delivery may include an inner secondary lumen that defines a fixed, non-circular transverse cross-sectional configuration (e.g., a non-circular inner contour (surface, shape)) that corresponds to the transverse cross-sectional configuration defined by the tertiary wire. The secondary delivery catheter may include an "over-the-wire" configuration, which allows for slidable insertion of the tertiary wire into the secondary delivery catheter such that the secondary delivery catheter is (at least partially) positioned about the tertiary wire. Due to the non-circular transverse cross-sectional configurations defined by the tertiary wire and the secondary delivery catheter, the tertiary wire is insertable into the secondary delivery catheter in a plurality of discrete (rotational) orientations, the number of which is determined by the particular configurations of the tertiary wire and the secondary delivery catheter. For example, in one particular embodiment, the tertiary wire and the secondary delivery catheter may include corresponding triangular transverse cross-sectional configurations, which facilitate insertion of the tertiary wire into the secondary delivery catheter in three distinct (rotational) orientations that are offset from each other by (approximately) 120°. The non-circular transverse cross-sectional configurations of the tertiary wire and the secondary delivery catheter allow the relative (rotational) orientations of the tertiary wire and the secondary delivery catheter to be maintained during advancement of the secondary delivery catheter through the blood vessel.

During use, the secondary delivery catheter is rotated into a predetermined orientation prior to insertion of the tertiary wire, which results in corresponding rotation of the secondary stent to allow for advancement of the secondary delivery catheter and the secondary stent into the blood vessel, and deployment of the secondary stent, in a predetermined (rotational) orientation.

In certain embodiments, the intravascular device may include at least one energy transfer component.

In another aspect of the present disclosure, a wire is disclosed for intraluminal use. The wire includes an anchor at a distal end thereof.

In certain embodiments, the anchor may include a branched wire segment. For example, the branched wire segment may split into at least two segments such that, upon the application of a predetermined radial force, the at least two segments are directed into walls of the blood vessel in different directions.

In certain embodiments, the at least one anchor may be configured such that the branched wire segment is moved from a first (insertion, inactive, collapsed) configuration, in which the at least two segments are positioned in generally adjacent relation, into a second (anchoring, active, expanded) configuration, in which the at least two segments are separated from each other to thereby anchor the primary wire within the blood vessel upon the application of an external stimulus. It is envisioned that the at least one anchor may be moved from the first configuration into the second configuration upon the application of any suitable stimulus (e.g., to a proximal end of the wire) including, for example, a thermal stimulus, an electric stimulus, a mechanical stimulus, a magnetic stimulus, a hydrostatic stimulus, etc.

In certain embodiments, the wire may further include a central segment that continues distally beyond the at least one anchor.

In another aspect of the present disclosure, an intravascular system is disclosed for treating of a blood vessel. The intravascular system includes a first catheter defining a first lumen and a first delivery device that is configured for insertion into the first lumen of the catheter. The first lumen terminates in a distal end hole and has a first non-circular transverse cross-sectional configuration. The first delivery device includes a first stent and a first elongated member that supports the first stent such that the first elongated member and the first stent are movable through the first lumen to facilitate delivery of the first stent to a target location within the blood vessel. The first elongated member has a second non-circular transverse cross-sectional configuration that corresponds to the first non-circular transverse cross-sectional configuration to thereby inhibit rotation of the first elongated member within the catheter and control orientation of the first stent relative to the catheter.

In certain embodiments, the delivery device may be configured as a packaging catheter. The packaging catheter can have an inner lumen that is substantially similar in dimensions to the inner lumen of the first catheter.

In certain embodiments, the packaging catheter component may further include a body and a pusher that supports the first stent. In such embodiments, the first elongated member is defined by the pusher and is configured for movement from the packaging catheter into the first lumen of the first catheter through the body, such that the pusher and the first stent are insertable into the blood vessel through the first catheter. In some embodiments, the pusher has a similar outer dimension to the corresponding inner dimension of the inner lumen of the first catheter, but slightly smaller, to allow longitudinal movement of the pusher and a mounted stent thereon, without allowing rotation.

In certain embodiments, the first stent may be configured for self-expansion such that the first stent automatically expands in the blood vessel upon exposure from the catheter.

In certain embodiments, the first delivery device may be configured as a balloon catheter including a first inflatable member. In such embodiments, the first elongated member is defined by a body of the balloon catheter such that the body of the balloon catheter is received by the first lumen of the catheter and the first stent is positioned about the first inflatable member such that the first stent is deployed upon inflation of the first inflatable member.

In certain embodiments, the first delivery device may include a second lumen that extends therethrough.

In certain embodiments, the second lumen may terminate in a side hole.

In certain embodiments, the second lumen may include a third non-circular transverse cross-sectional configuration.

In certain embodiments, the intravascular system may further include a second delivery device that is configured for insertion into the second lumen of the first delivery device.

In certain embodiments, the second delivery device may include a second stent and a second elongated member that supports the second stent such that the second elongated member and the second stent are movable through the second lumen to facilitate delivery of the second stent through the side-hole to treat a side branch of the blood vessel.

In certain embodiments, the second elongated member may have a fourth non-circular transverse cross-sectional configuration that corresponds to the third non-circular transverse cross-sectional configuration to thereby inhibit rotation of the second elongated member within the first delivery device and control orientation of the second stent relative to the catheter.

In certain embodiments, the second stent may be configured for self-expansion such that the second stent automatically expands upon exposure in the blood vessel.

In certain embodiments, the second delivery device may further include an inflatable member that is supported by the second elongated member. In such embodiments, the second stent is supported by the inflatable member such that the second stent is deployed upon inflation of the inflatable member.

In another aspect of the present disclosure, an intravascular system is disclosed for treating of a blood vessel. The intravascular system includes a first medical device and a second medical device. The first medical device includes: an elongated member; a first inflatable member that is supported by the elongated member; and a first stent that is supported by the first inflatable member such that the first stent is deployed upon inflation of the first inflatable member. The elongated member defines a first lumen that extending from a proximal end hole to a distal end hole and a second lumen that extends in generally parallel relation to the first lumen from the proximal end hole to a side-hole that is located proximally of the distal end hole. The first inflatable member includes a first fenestration and the first stent includes a second fenestration. The second medical device is configured for insertion into the second lumen to access a side branch of the blood vessel through the side-hole, through the first fenestration in the first inflatable member, and through the second fenestration in the first stent.

In certain embodiments, the second medical device is configured as a packaging catheter.

In certain embodiments, the packaging catheter may include: a body that is configured for connection to the first medical device; a pusher that is configured for movement through the body; and a second stent that is supported on the pusher such that the pusher and the second stent are insertable into the side branch of the blood vessel through the first medical device via the second lumen and the side-hole.

In certain embodiments, the second stent may be configured for self-expansion such that the second stent automatically expands in the side branch of the blood vessel upon exposure from the side-hole.

In certain embodiments, the second lumen may define a first non-circular transverse cross-sectional configuration and the pusher defines a second non-circular transverse cross-sectional configuration corresponding to the first non-circular transverse cross-sectional configuration so as to inhibit rotation of the pusher and the second stent within the second lumen to thereby control orientation of the second stent relative to the first medical device.

In certain embodiments, the first non-circular transverse cross-sectional configuration and the second non-circular transverse cross-sectional configuration may each be defined by a plurality of linear segments.

In certain embodiments, the first non-circular transverse cross-sectional configuration and the second non-circular transverse cross-sectional configuration may be such that the pusher is insertable into the second lumen in at least three distinct (rotational) orientations.

In some embodiments, least one of the hub, first catheter, first elongated member, and medical device has at least one marker at a set circumferential rotation. In other embodiments, at least two or more of the hub, first catheter, first elongated member and medical device has one has at least one marker. In some embodiments, two or more of the markers are at a substantially same circumferential rotation. In certain embodiments, the second medical device may be configured as a guide wire.

In certain embodiments, the guide wire may be insertable into the side branch of the blood vessel through the side-hole in the first medical device.

In certain embodiments, the second medical device may be configured as a balloon catheter.

In certain embodiments, the balloon catheter may include: a body; a second inflatable member that is supported by the body; and a second stent that is supported by the second inflatable member such that the second stent is deployed upon inflation of the second inflatable member.

In certain embodiments, the body of the balloon catheter may define a lumen that is configured to receive a guide wire such that the balloon catheter is insertable into the side branch of the blood vessel over the guide wire.

In certain embodiments, the second lumen may define a first non-circular transverse cross-sectional configuration and the body of the balloon catheter may define a second non-circular transverse cross-sectional configuration that corresponds to the first non-circular transverse cross-sectional configuration to thereby inhibit rotation of the balloon catheter and the second stent within the second lumen and control orientation of the second stent relative to the first medical device.

In another aspect of the present disclosure, a system is disclosed for maintaining an orientation of a stent during delivery. The system includes a first medical device supporting the stent and a second medical device that is configured to receive the first medical device. The first medical device and the second medical device include corresponding non-circular transverse cross-sectional configurations to inhibit rotation of the first medical device within the second medical device and thereby control orientation of the stent.

In certain embodiments, the first medical device may be configured as a balloon catheter that includes an inflatable member. In such embodiments, the stent is supported by the inflatable member such that the stent is deployed upon inflation of the inflatable member.

In certain embodiments, the stent may be configured for self-expansion such that the stent automatically expands upon exposure from the second medical device.

In certain embodiments stents can be delivered sequentially as well. For example, a first catheter with a first non-circular inner lumen configuration of the system can be inserted into a vessel, beyond a branch orifice. A packaging catheter with a substantially similar inner lumen includes a first elongated member defined by a pusher, which has a similar outer dimension to the corresponding inner dimensions of the inner lumen, but slightly smaller, to allow longitudinal movement of the pusher and a mounted stent thereon, without allowing rotation. Additionally, the first catheter can have a proximal hub with a shape that corresponds to the outer shape of at least the distal segment of the packaging catheter, such that the packaging catheter can be inserted into the hub in a known orientation, and the inner lumen of the packaging catheter will then align with the orientation of the inner lumen of the proximal segment of the first catheter. A stent with a fenestration of a similar size as the orifice of the side branch can be mounted on the pusher wire, and can be delivered through the packaging catheter lumen and the first catheter lumen over the pusher, without rotating within the catheters. A stent preloaded into the packaging catheter in the correct orientation of the fenestration relative to the orifice of the side branch, with or without the aid of any rotation of the packaging catheter relative to the primary catheter and its hub, will then be delivered with the pusher from the packaging catheter and into the first catheter. The stent can then be delivered across the orifice of the side branch, and deployed with the fenestration overlying the orifice, by unsheathing the first catheter from the pusher and stent. The stent expands upon release from the constraints of the catheter. The stent can optionally be resheathable and/or detachable from the pusher, allowing the stent to be repositioned if desired before it is permanently implanted.

In some embodiments, least one of the hub, first catheter, first elongated member, and medical device has at least one marker at a set circumferential rotation. In other embodiments, at least two or more of the hub, first catheter, first elongated member and medical device has one has at least one marker. In some embodiments, the markers are at a substantially same circumferential rotation.

In some embodiments, the first delivery device comprises a packaging catheter including a second lumen, wherein the second lumen has a substantially similar shape as the first lumen, so that when the first elongate member and the first medical device are transferred from the packaging catheter to the first catheter, a cross-sectional configuration of the first catheter and first lumen, a cross-sectional configuration of the packaging catheter and the second lumen, and an outer transverse cross-sectional configuration of the first elongated member inhibit rotation of the first medical device during pushing through the packaging catheter, transfer from the packaging catheter to the first catheter, and pushing through the first catheter for subsequent delivery to a target treatment area.

In some embodiments, a hub is at a proximal end of the first catheter, wherein an inner shape of the hub and an outer shape of the distal end of the first catheter are configured in corresponding noncircular shapes so that a distal end of the delivery catheter can be inserted into the hub to thereby inhibit rotation of the packaging catheter relative to the first catheter, and thereby facilitate transfer of the first elongated member within the delivery catheter and during transfer to the first catheter and control orientation of the first medical device relative to the first catheter.

In some embodiments, a second medical device is configured as a second catheter and includes a body configured for connection to the first medical device and passage through the second lumen and a wire configured for passage through the second lumen through the first and second fenestrations and into a side branch or a side lesion, wherein the distal end-hole of the second catheter can be advanced from the second lumen, through the side hole, first and second fenestrations, and into the side branch or side lesion over the wire.

The second medical can be supported on a pusher such that the pusher and the second medical device are insertable into the side branch of the blood vessel through the second catheter, after removal or the wire, via the second lumen and the side-hole. In some embodiments, the second medical device is a stent, configured for self-expansion such that the second medical device automatically expands in the side branch of the blood vessel upon exposure from the second catheter.

In some embodiments, the second lumen defines a non-circular transverse cross-sectional configuration and an outer surface of the second medical device defines a non-circular transverse cross-sectional configuration corresponding to the non-circular transverse cross-sectional configuration of the second lumen so as to inhibit rotation of the second medical device.

In some embodiments, the inner lumen of the second catheter defines a non-circular transverse cross-sectional configuration and the outer surface of the pusher defines a non-circular transverse cross-sectional configuration corresponding to the non-circular transverse cross-sectional configuration of the second catheter so as to inhibit rotation of the pusher and the second medical device within the second lumen to thereby control orientation of the second medical device relative to the first medical device.

In some embodiments, the elongated member is removed after the first stent has been deployed.

In some embodiments, the second lumen defines a non-circular transverse cross-sectional configuration and an outer surface of a majority of the wire, including a proximal end outside the patient's body, or of a working segment, defines a non-circular transverse cross-sectional configuration corresponding to the non-circular transverse cross-sectional configuration of the second lumen to thereby inhibit rotation of the wire within the second lumen.

In some embodiments, a substantially similarly corresponding dimensioned inner diameter of a third medical device inhibits rotation of the balloon catheter and the second stent over the wire and controls orientation of the second stent relative to the vascular anatomy and/or the first medical device.

DESCRIPTION OF THE DRAWINGS

Throughout the present disclosure, the term "vascular abnormality" should be understood to include aneurysms, lesions, fistulas, ruptures, and any other such malformation in a blood vessel, as well as normal vascular structures that can sometimes require closure or other coverage, including but not limited to the left atrial appendage.

Additionally, the term "medical device" should be understood to include any of the catheters, wires, or other such structures (or components of such structures) described herein and the term "elongated member" should be understood to include any elongated structure (e.g., tube, wire, catheter body, or the like) described herein.

FIGS. 7A-7D are transverse, cross-sectional views illustrating a variety of non-circular cross-sectional configurations for the lumen extending through the primary delivery catheter according to various embodiments of the present disclosure.

FIG. 7E is a perspective view of an alternate embodiment of the primary delivery catheter, which includes a variety of markers (e.g., radiopaque markers) that are located in a variety of (rotational) positions to facilitate external visualization of the primary delivery catheter.

FIG. 8 is perspective view of the pusher.

FIG. 9 is a perspective view of the packaging catheter.

FIG. 16 is a longitudinal, cross-sectional view illustrating deployment of the primary delivery catheter into the blood vessel via the guide wire to treat the vascular abnormality according to one aspect of the present disclosure.

FIG. 17 is a longitudinal, cross-sectional view illustrating insertion of the pusher and the primary stent through the primary delivery catheter.

FIG. 18 is a longitudinal, cross-sectional view illustrating an alternate embodiment of the intravascular system.

FIG. 19 is a transverse, cross-sectional view taken through line 19-19 in FIG. 18.

FIG. 20 is a longitudinal, cross-sectional view illustrating deployment of a self-expanding secondary stent into a side branch of the blood vessel through a primary delivery catheter and a first delivery device.

FIG. 21 is a transverse, cross-sectional view taken through line 21-21 in FIG. 20.

Figure 1A:
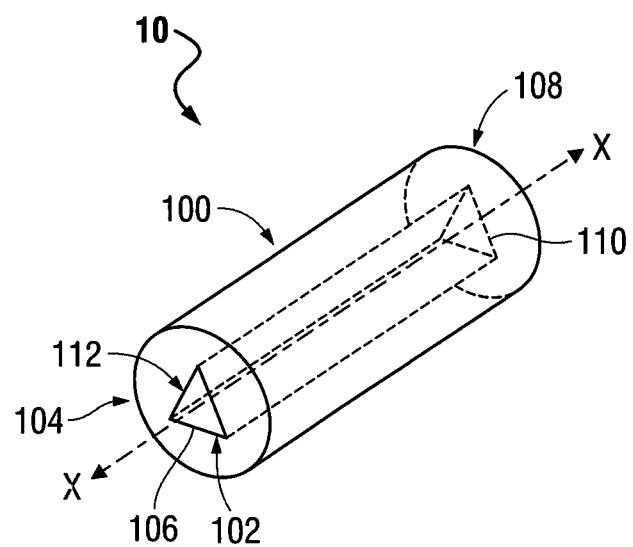
FIG. 1A is a perspective view of an intravascular system including a primary delivery catheter.

Further elaborating on the brief description provided above, FIG. 1A provides a perspective view of an intravascular system 10 for the treatment of an anatomical vessel (e.g., a blood vessel V (FIG. 2A)). In the embodiment illustrated, the intravascular system 10 includes a delivery catheter 100 including an elongated body (member) 102 that extends along a longitudinal axis X. The body 102 includes a proximal (first) end 104 defining a proximal end hole 106, a distal (second) end 108 defining a distal end hole 110, and a (generally) cylindrical outer transverse cross-sectional configuration. A lumen 112 extends through the body 102 from the proximal end 104 to the distal end 108 and defines a non-circular transverse (lateral) cross-sectional configuration. More specifically, in the particular embodiment illustrated, the lumen 112 defines a (generally) triangular transverse (lateral) cross-sectional configuration. As described below, however, a variety of other non-circular transverse (lateral) cross-sectional configurations are also contemplated by the present disclosure including, for example, rectangles, pentagons, hexagons, octagons, squares, ovals, ellipse, stars, etc.

It should be appreciated that in the embodiments described herein, a stent is delivered by the catheter/system; however the catheter system can be utilized with other medical devices (the stent providing just one example).

The delivery catheter 100 is configured to deliver an occlusion device 200 (FIG. 2C) (e.g., a stent 202) or other medical device to a target site within the blood vessel V (or other such location within a patient's vasculature). As elaborated upon below, in certain embodiments, the occlusion device 200 may be carried (or otherwise supported) by an inflatable balloon (or other such member) that is connected to the delivery catheter 100. Alternatively, the occlusion device 200 may be carried (or otherwise supported) by a separate delivery device.

In one embodiment, for example, it is envisioned that the delivery device may be configured as a packaging catheter 300 (FIG. 2A) that includes an elongated pusher 302 (e.g., a wire) with a proximal end 304 and a distal end 306 that carries (or otherwise supports) the stent 202 in either a fixed or releasable (disconnectable) manner. For example, it is envisioned that the stent 202 may be pre-loaded and crimped (or otherwise secured) to the distal end 306 of the pusher 302 such that the stent 202 can be separated from the pusher 302 and deployed within the vasculature. In such embodiments, the packaging catheter 300 is pre-loaded with the pusher 302 and the stent 202 and the packaging catheter 300 is connected to the delivery catheter 100 (either directly or indirectly) such that, via axial movement of the pusher 302, the stent 202 is deliverable from the packaging catheter 300, into and through the delivery catheter 100, and into the blood vessel V.

In an alternate embodiment, it is envisioned that the delivery device may be configured as a secondary catheter (e.g., a balloon catheter 400 (FIG. 2B) or a hypotube) that is configured for insertion into the blood vessel V (FIG. 2A) through the delivery catheter 100. In such embodiments, the stent 202 may be supported on an inflatable member 406 (e.g., a balloon or other such suitable structure) of the balloon catheter 400 and deployed via expansion of the inflatable member 406. In such embodiments, it is envisioned that the balloon catheter 400 may be inserted through the delivery catheter 100 over a guide (delivery) wire 500 that extends into the blood vessel V.

Control over, and proper positioning of, the stent 202 is facilitated by inhibiting (if not entirely preventing) relative rotation between the stent 202 and the delivery catheter 100. For example, when the delivery catheter 100 is used in connection with the packaging catheter 300, the pusher 302 will include a non-circular (transverse) cross-sectional configuration (e.g., a cross-sectional configuration that is generally orthogonal in relation to a longitudinal axis of the pusher 302) corresponding to that defined by the lumen 112 of the delivery catheter 100 to limit (if not entirely prevent) rotation of the pusher 302 within the delivery catheter 100, thereby facilitating control over the (rotational) orientation of the stent 202 via manipulation of the delivery catheter 100 (and/or the pusher 302). Similarly, when the delivery catheter 100 is used in connection with the aforementioned balloon catheter 400, the balloon catheter 400 will include an outer (transverse) non-circular transverse cross-sectional configuration (e.g., a cross-sectional configuration that is generally orthogonal in relation to a longitudinal axis of the balloon catheter 400) corresponding to that defined by the lumen 112 to limit (if not entirely prevent) rotation of the balloon catheter 400 within the delivery catheter 100, thereby facilitating control over the (rotational) orientation of the stent 202 via manipulation of the balloon catheter 400 (and/or the delivery catheter 100). Regardless of the particular method of placement and the medical devices used, it should be appreciated that the configurations of the delivery catheter 100, the pusher 302, and the balloon catheter 400 are such that the pusher 302 and the balloon catheter 400 are axially movable (slidable) through the delivery catheter 100 so as not to interfere with advancement of the pusher 302 and the balloon catheter 400 into the vasculature.

Thus the pusher is configured for movement from the packaging catheter into the lumen of the delivery catheter through the body, such that the pusher and the stent are insertable into the blood vessel through the delivery catheter. In some embodiments, the pusher has a similar outer dimension to the corresponding inner dimension of the inner lumen of the delivery catheter, but slightly smaller, to allow longitudinal movement of the pusher and a mounted stent thereon, without allowing rotation.

Upon positioning of the delivery catheter 100 within the vasculature (e.g., the blood vessel V), imaging can be used to confirm the orientation of the distal end 108 of the delivery catheter 100 relative to the proximal end 104 of the delivery catheter 100. For example, it is envisioned that the respective proximal and distal ends 104, 108 of the delivery catheter 100 may include corresponding markers 114 (e.g., radiopaque markers) that are positioned in corresponding locations (e.g., at "12 o'clock" locations), as elaborated upon below. Subsequent imaging with x-ray, 3-D x-rays, CT imaging, echocardiography, ultrasound, IVUS, or other modalities can then confirm the relative (rotational) position of the distal end 108 of the delivery catheter 100 (e.g., at, near, or adjacent to the vascular abnormality (e.g., the an aneurysm A) relative to the proximal end 104 of the delivery catheter 100 to ascertain the extent to which the distal end 108 of the delivery catheter 100 is rotationally offset from the proximal end 104 (e.g., as a result of twisting or other such deflection experienced by the delivery catheter 100 during navigation through the vasculature). When employed, the delivery device (e.g., the pusher 302, the balloon catheter 400, etc.) and, thus, the stent 202, can then be rotated a corresponding amount prior to insertion into the delivery catheter 100 to account for the observed degree of (rotational) offset of the distal end 108 of the delivery catheter 100, thereby facilitating accurate orientation and deployment of the stent 202. Fundamentally, in somewhat tortuous anatomy, most known catheters, wires, and stents cannot be accurately rotated at the target site from the proximal end (hub) of the device. However, the present disclosure relies on a fixed degree of random rotation during initial delivery of the guide (delivery) wire 500, the delivery catheter 300, etc., to be recorded accurately and subsequently accounted for, allowing for accurate orientation, delivery, and placement of the stent 202. In some cases, trial retrievable stent devices or similar devices can also be used to determine or confirm the orientation of the guide wire, the delivery catheter 300, etc., at the target site in the vasculature.

Figure 1B:
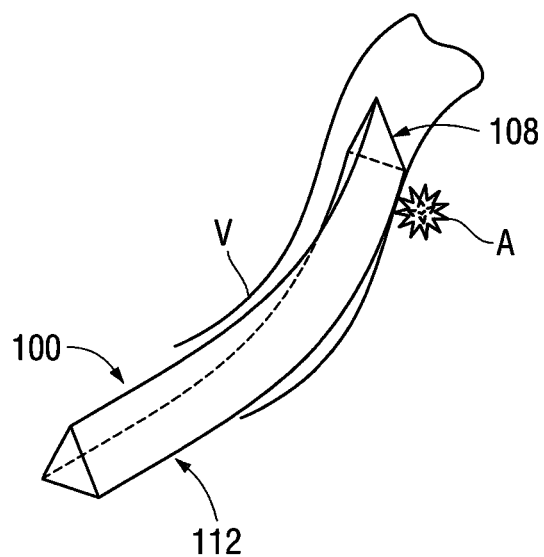
FIG. 1B is a (partial) perspective view of a lumen of the primary delivery catheter seen in FIG. 1A shown positioned within an anatomical vessel (e.g., a blood vessel).

FIG. 1B provides a (partial) view of the delivery catheter 100 positioned within the blood vessel V such that the distal end 108 is located in proximity (e.g., at or adjacent) to the vascular abnormality (e.g., the aneurysm A) that is the subject of the medical procedure. For simplicity and clarity, only the lumen 112 of the delivery catheter 100 is illustrated.

Figure 1C:
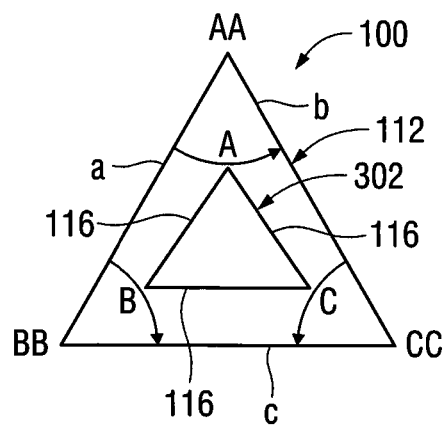
FIG. 1C is a (partial) transverse, cross-sectional view of a delivery device (e.g., a pusher of a packaging catheter) positioned within the lumen of the primary delivery catheter and shown in a first (rotational) position.

FIG. 1C is a (partial) cross-sectional view of the delivery catheter 100 taken transversely (e.g., orthogonally) in relation to the longitudinal axis X (FIG. 1A) and shown with the pusher 302 of the packaging catheter 300 positioned within the lumen 112 in a first orientation.

Figure 1D:
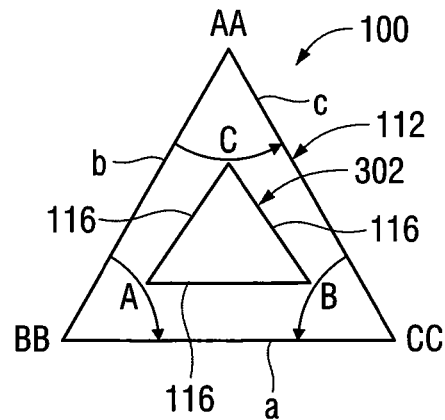
FIG. 1D is a (partial) transverse, cross-sectional view of the pusher positioned within the lumen of the primary delivery catheter and shown in a second (rotational) position.

FIG. 1D is a (partial) cross-sectional view of the delivery catheter 100 and the pusher 302 shown positioned within the lumen 112 in second first orientation that is (rotationally) offset from the first orientation seen in FIG. 1C by (approximately) 120°.

Although shown as a solid wire 308 (FIG. 2A) in the illustrated embodiment, it should be appreciated that alternate configurations for the pusher 302 are also envisioned herein. For example, it is envisioned that the pusher 302 may define a lumen therethrough (e.g., to facilitate receipt of the aforementioned 114 such that the pusher 302 is advanceable into the blood vessel V in an "over-the-wire" configuration).

Figure 2A:
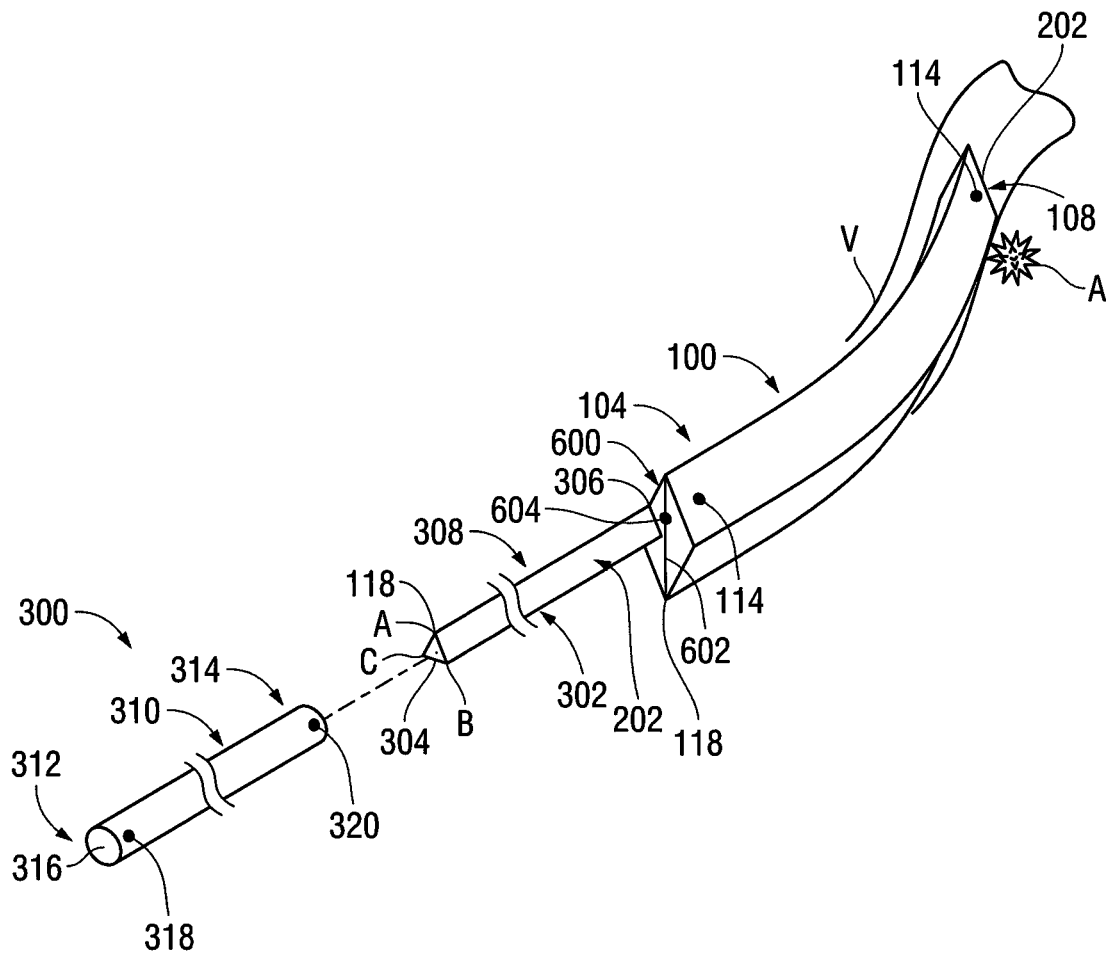
FIG. 2A is a perspective view of the packaging catheter and the primary delivery catheter during treatment of a vascular abnormality in a blood vessel.
Figure 2B:
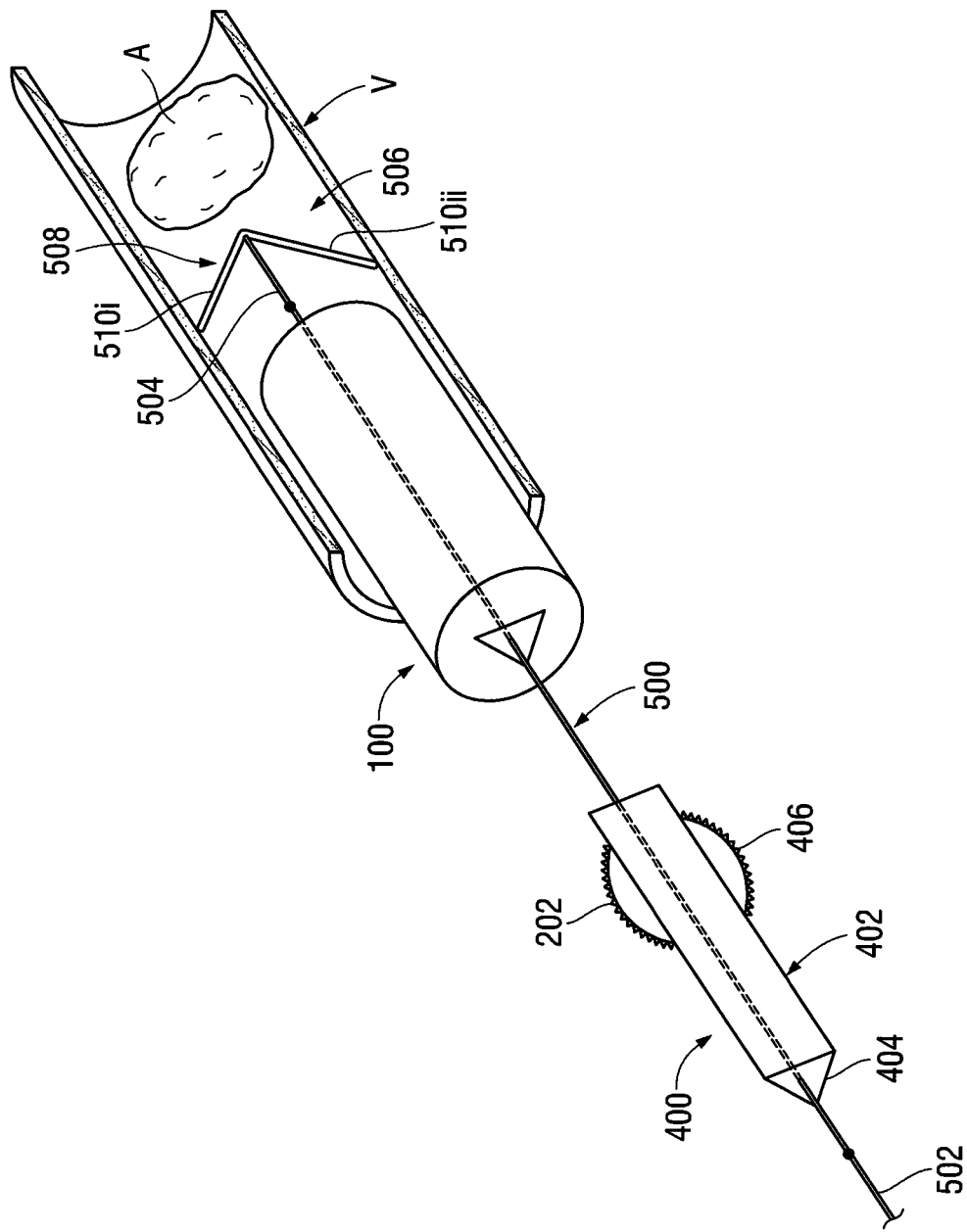
FIG. 2B is a perspective view of the primary delivery catheter shown in connection with an alternate embodiment of the delivery device, which is configured as a balloon catheter, during treatment of the vascular abnormality.
Figure 2C:
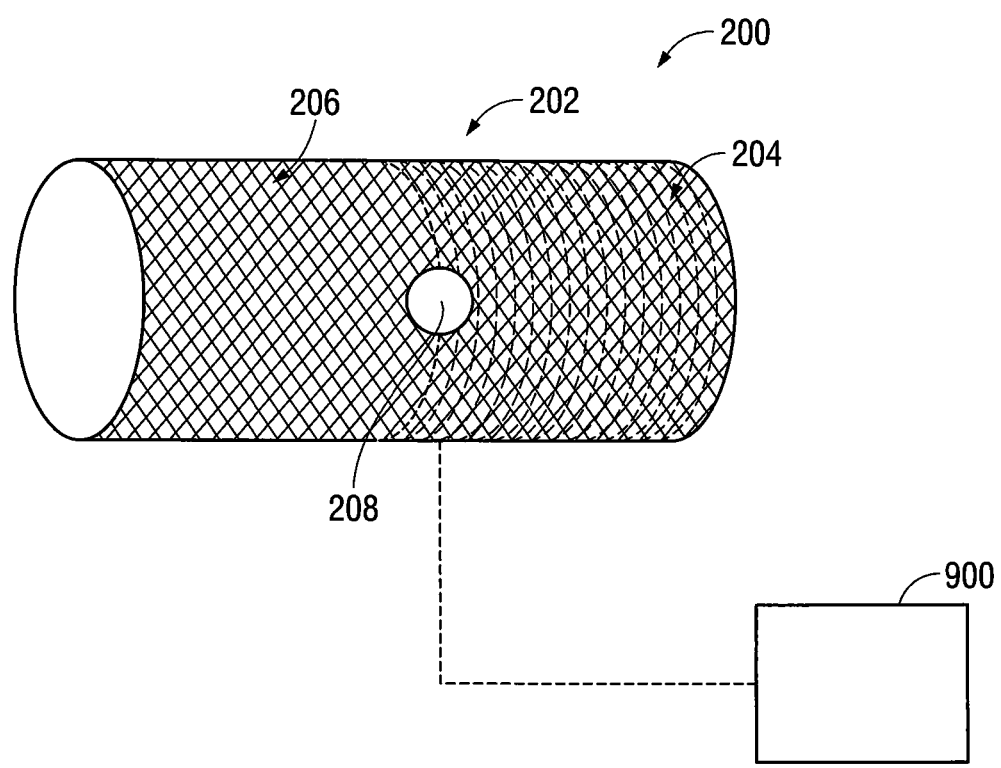
FIG. 2C is a perspective view of a primary stent (or other such occlusion device) that is positionable within the blood vessel via the delivery device and the primary delivery catheter to treat the vascular abnormality.

In the particular embodiment seen in FIG. 2C, the stent 202 includes a self-expanding, differentially porous configuration with a first (covered) region 204 having a first porosity and a second (uncovered) region 206 having a second, different (e.g., greater) porosity. In certain embodiments, it is envisioned that the first region 204 may be completely impermeable to fluid, blood, etc., and/or that the second region 206 may be devoid of struts (threads, etc.) such that the second region 206 includes or otherwise defines one or more fenestrations 208, holes, apertures, or other such openings in the stent 202.

The present disclosure contemplates a variety of geometrical configurations for the stent 202 (or other medical devices) including, for example, both (generally) circular transverse cross-sectional configurations (e.g., so as to correspond to the (generally) circular transverse cross-sectional configuration of blood vessels), as seen in FIG. 2C, for example, and non-circular transverse cross-sectional configurations (e.g., to facilitate placement and/or anchoring of the stent 202 within the vasculature).

With reference to FIG. 1C, as mentioned above, the pusher 302 includes a non-circular transverse (lateral) cross-sectional configuration corresponding to that defined by the lumen 112 of the delivery catheter. More specifically, in the particular embodiment illustrated, the pusher 302 includes a (generally) triangular transverse (lateral) cross-sectional configuration. As discussed above (and elaborated upon below) in connection with the lumen 112, a variety of other non-circular transverse (lateral) cross-sectional configurations for the pusher 302 are also contemplated by the present disclosure. The corresponding non-circular transverse cross-sectional configurations defined by the lumen 112 of the delivery catheter and the pusher 302 allow for receipt of the pusher 302 in a manner that allows for longitudinal (axial) movement (e.g., sliding) of the pusher 302 through the delivery catheter 100 while inhibiting (if not entirely preventing) rotation of the pusher 302 within the delivery catheter 100 to thereby facilitate control over the orientation of the pusher 302 and, thus, the stent 202, relative to the delivery catheter 100.

While discussed in connection with the pusher 302, it should be appreciated that the anti-rotation principles attributable to the non-circular transverse (lateral) cross-sectional configuration are equally applicable to the balloon catheter 400, the guide wire, or other such medical device inserted into the patient's vasculature.

The triangular cross-sectional configuration of the lumen 112 is defined by three linear segments a, b, c that intersect to define vertices vertexes AA, BB, and CC and interior angles A, B, C of (approximately) 120°. For the purposes of nomenclature, counterclockwise rotation of the delivery catheter 100 by (approximately) 120° will results in positioning of the delivery catheter 100 (and, thus, the pusher 302) in the manner illustrated in FIG. 1D. It should be appreciated, however, that the number of linear segments may be varied in alternate embodiment so as to define any suitable non-circular (transverse) cross-sectional configuration for the lumen 112 (e.g., four segments, five segments, six segments, etc.).

The non-circular (transverse) cross-sectional configuration of the lumen 112 allows for insertion of the pusher 302 (or the balloon catheter 400) in a plurality of discrete (rotational) orientations. For example, in the illustrated embodiment, the triangular transverse cross-sectional configuration of the lumen 112 allows for receipt of the pusher 302 and, thus, the stent 202, in one of three discrete (rotational) orientations that are offset from each other by (approximately) 120°. Variability in the (rotational) orientation of the pusher 302 and the stent 202 allows for and accommodates (rotational) displacement experienced by the distal end 108 of the delivery catheter 100 (relative to the proximal end 104 and the aforementioned aneurysm A) during insertion into the blood vessel V by virtue of the tortuous nature of the vasculature. For example, if no (rotational) offset is observed between the distal end 108 of the delivery catheter 100 and the proximal end 104 (and the aneurysm A) (e.g., such that the distal end 108 and the proximal end 104 each remain in an initial "12 o'clock" position), the pusher 302 (or the balloon catheter 400) may be inserted in one (rotational) orientation (e.g., in a corresponding "12 o'clock" position). However, if a (rotational) offset is observed between the distal end 108 of the delivery catheter 100 and the proximal end 104 (and the aneurysm A), depending on the observed degree of (rotational) offset, the pusher 302 (or the balloon catheter 400) may be inserted in one of a plurality of different (rotational) orientations, which, in the illustrated embodiment, are (rotationally) offset from each other by (approximately) 120°, such that the stent 202 may be positioned in the blood vessel V as necessary or desired to treat the aneurysm A.

To facilitate observation of the (rotational) orientations of the distal end 108 of the delivery catheter 100, the pusher 302, the balloon catheter 400, the stent 202, etc., the delivery catheter 100, the pusher 302, the balloon catheter 400, the stent 202, etc., may include one or more markers (e.g. radiopaque markers), as discussed in further detail below, which may be visualized using any suitable technique such as, for example, x-ray, 3-D x-rays, CT imaging, echocardiography, ultrasound, IVUS, etc.

FIG. 2A illustrates the packaging catheter 300 and the delivery catheter 100 which, in the illustrated embodiment, are separated by a hub 600 having a port 602 such that the hub 600 is located between the delivery catheter 100 and the packaging catheter 300. It is envisioned that the hub 600 may a component of the packaging catheter 300 or the delivery catheter 100. Alternatively, it is envisioned that the hub 600 may be a discrete (free-standing) component of the intravascular system 10 that is configured to interface (connect, engage) with the packaging catheter 300 and/or the delivery catheter 100 such that the packaging catheter 300 and the delivery catheter 100 are indirectly connected via the hub 600.

The packaging catheter 300 includes an elongated tubular body 310 having respective proximal and distal ends 312, 314 and defining a lumen 316 that is configured to receive the pusher 302 and the stent 202. The hub 600 is configured for releasable connection to the proximal end 104 of the delivery catheter 100 (e.g., via a corresponding hub on the delivery catheter 100) such that the pusher 302 and the stent 202 are insertable through the port 602 in the hub 600, into the lumen 112 of the delivery catheter 100, and into proximity (e.g., at or adjacent) to the aneurysm A. It is envisioned that the distal end 306 of the packaging catheter 300 and the proximal end 104 of the delivery catheter 100 may be disposed within the hub 600 in (general) alignment to facilitate movement of the pusher 302 from the elongated body 310 of the packaging catheter 300 into the lumen 112 of the delivery catheter 100.

In one method of use (seen in FIG. 2A), the delivery catheter 100 is advanced through the blood vessel V to the target site (e.g., such that the distal end 108 of the delivery catheter 100 is located in proximity (e.g., at or adjacent) to the aneurysm A). The stent 202, which is pre-loaded on the pusher 302, may be then be advanced through the delivery catheter 100 into the blood vessel V (e.g., via the an elongated body 310 of the packaging catheter 300 and the hub 600) such that the stent 202 is automatically expanded (deployed) upon exposure from the delivery catheter 100.

FIG. 2B illustrates insertion of the balloon catheter 400 and the stent 202 into the blood vessel V through the delivery catheter 100. As seen in FIG. 2B, the balloon catheter 400 includes an elongated (tubular) body (member) 402 defining a lumen 404 and an inflatable member 406 that is supported by the elongated body 402. The stent 202 is positioned about (secured to) the inflatable member 406 (e.g., via crimping) such that the stent 202 is deployed via expansion (inflation) of the inflatable member 406.

To facilitate proper placement of the balloon catheter 400 and the stent 202, the guide wire 500, which includes respective proximal and distal ends 502, 504, is positioned within the blood vessel 100 such that the guide wire 500 is located in proximity (e.g., at or adjacent) to the aneurysm A.

The balloon catheter 400 is then advanced into the blood vessel V over the guide wire 500 (e.g., through the lumen 112 in the delivery catheter 100) such that the guide wire 500 extends through the lumen 404 defined by the elongated body 402 of the balloon catheter 400.

To facilitate control over, and proper positioning of, the stent 202, as indicated above, the balloon catheter 400 includes (defines) a non-circular transverse (e.g., triangular) cross-sectional configuration corresponding to that defined by the lumen 112 of the delivery catheter 300 to inhibit (if not entirely prevent) relative rotation between the balloon catheter 400 and the delivery catheter 300, thereby facilitating control over the (rotational) orientation of the stent 202 via manipulation of the balloon catheter 400.

To further facilitate control over the (rotational) orientation of the stent 202, in certain embodiments, it is envisioned that the lumen 404 of the balloon catheter 400 may include a non-circular transverse (e.g., triangular) cross-sectional configuration corresponding to that defined by the guide wire 500 to inhibit (if not entirely prevent) relative rotation between the balloon catheter 400 and the guide wire 500.

To secure the guide wire 500 within the blood vessel V, in certain embodiments, it is envisioned that the guide wire 500 may include one or more stability components such as anchors 506 at (or adjacent to) the distal end 504 thereof. In the particular embodiment seen in FIG. 2B, for example, the anchor 506 includes a branched wire segment 508 that defines a plurality of segments 510 (e.g., a first segment 510*i* and a second segment 510*i*). Upon the application of a predetermined radial force to the anchor 506, the segments 510 are directed into the wall of the blood vessel V in different directions.

It is envisioned that the anchor(s) 506 may be configured such that the branched wire segment 508 is moved from a first (insertion, inactive, collapsed) configuration, in which the segments 510 are positioned in generally adjacent relation to each other and to the distal end 504 of the guide wire 500, into a second (anchoring, active, expanded) configuration, in which the segments 510 are separated from each other to thereby anchor the guide wire 500 within the blood vessel V upon the application of an external stimulus. It is envisioned that the at least one anchor 506 may be moved from the first configuration into the second configuration upon the application of any suitable stimulus including, for example, a thermal stimulus, an electric stimulus, a mechanical stimulus, a magnetic stimulus, a hydrostatic stimulus, etc.

In various embodiments of the disclosure, it is envisioned that the configuration of the anchor(s) 506 may be varied. For example, it is envisioned that the anchor(s) 506 may include a tortuous (e.g., a spring-like) configuration. Additionally, or alternatively, it is envisioned that the anchor(s) 506 may include a balled wire, a retrievable stent, or any other structure suitable for the intended purpose of securing the guide wire 500 in relation to the blood vessel V (e.g., to maintain the (rotational) position of the distal end 504 of the guide wire 500).

In some embodiments, the guidewire has at least one segment that comprises at least two wires that when detached from a detachment zone (such as via the detachment methods described herein, or by other methods), the wire will splay and apply pressure to the side walls of the vessel, and thereby help anchor the wire in place. This will minimize longitudinal movement and/or rotational movement. The guidewire in some embodiments, can have a non-circular outer shape along a majority of its length, starting at its proximal end outside the patient's body, and can have at least one marker to define a circumferential position. This stability component of the wire at the distal end, preferably distal to the intended deployment site of the device, stabilizes the rotational orientation of the wire and prevents its rotation during device delivery.

It should be appreciated that the discussion above concerning the anchor(s) 506 is applicable to any of the guide wires (or embodiments thereof) described herein.

Figure 3:
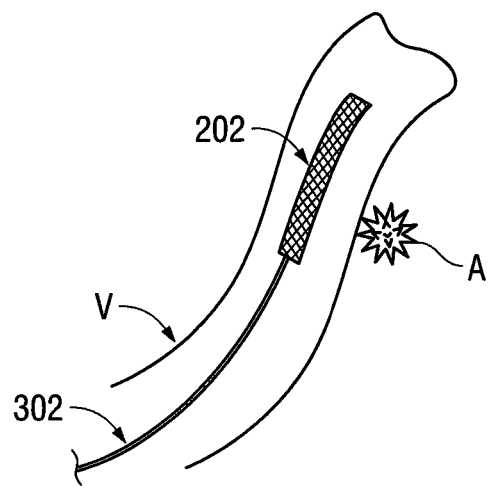
FIG. 3 is a perspective view illustrating advancement of the primary stent through the blood vessel via the pusher during treatment of the vascular abnormality.

With reference to FIG. 3, the pusher 302 and the stent 202 are illustrated and shown located within the blood vessel V following removal of the delivery catheter 100. In certain embodiments, it is envisioned that the distal end 306 of the pusher 302 may extend distally beyond the stent 202 or, alternatively, that the distal end 306 of the pusher 302 may be coterminous with the stent 202 such that the distal end 306 of the pusher 302 does not extend distally beyond the stent 202, as seen in FIG. 3.

Figure 4:
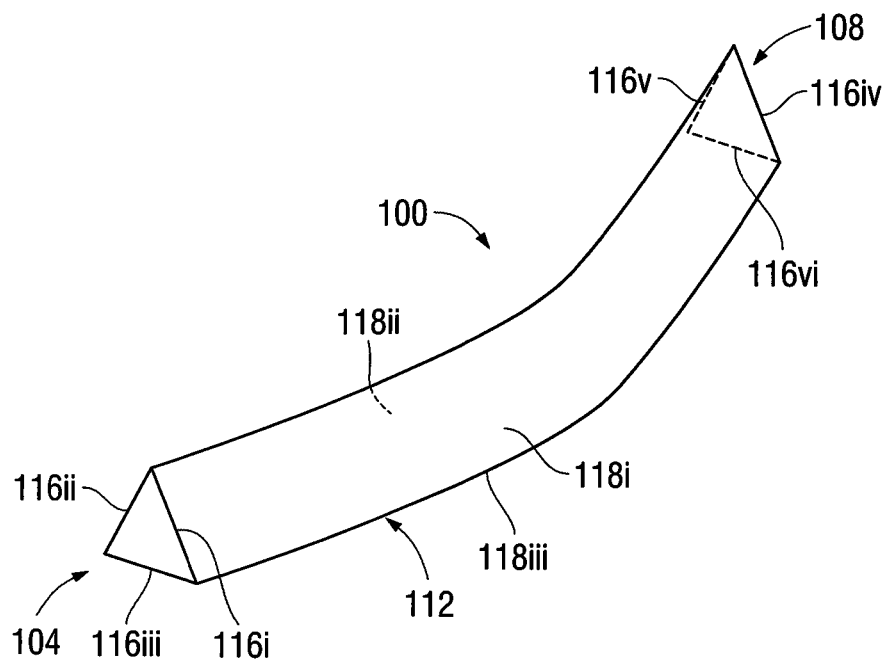
FIG. 4 is a (partial) perspective view of the primary delivery catheter.

FIG. 4 provides a (partial) a view of the delivery catheter 100. For simplicity and clarity, only the lumen 112 of the delivery catheter 100 is illustrated. As seen in FIG. 4, the triangular transverse cross-sectional configuration of the lumen 112 defines three linear segments (sides) 116, which are identified at the proximal end 104 of the delivery catheter 100 by the reference characters 114*i*, 114*ii*, 114*iii* and at the distal end 108 of the delivery catheter 100 by the reference characters 114*iv*, 114*v*, 114*vi*. As seen in FIG. 4, a linear face 118*i* extends between segments 114*i*, 114*iv*, a linear face 118*ii* extends between segments 114*ii*, 114*vi*, and a linear face 118*iii* extends between segments 114*iii*, 114*vi* along the axial length of the delivery catheter 100. Although shows as being triangular in configuration, it should be appreciated that alternative embodiments (not shown) may employ other non-circular cross-sectional configurations, such as, for example, rectangles, pentagons, hexagons, octagons, squares, ovals, ellipse, stars, etc.

Figure 5:
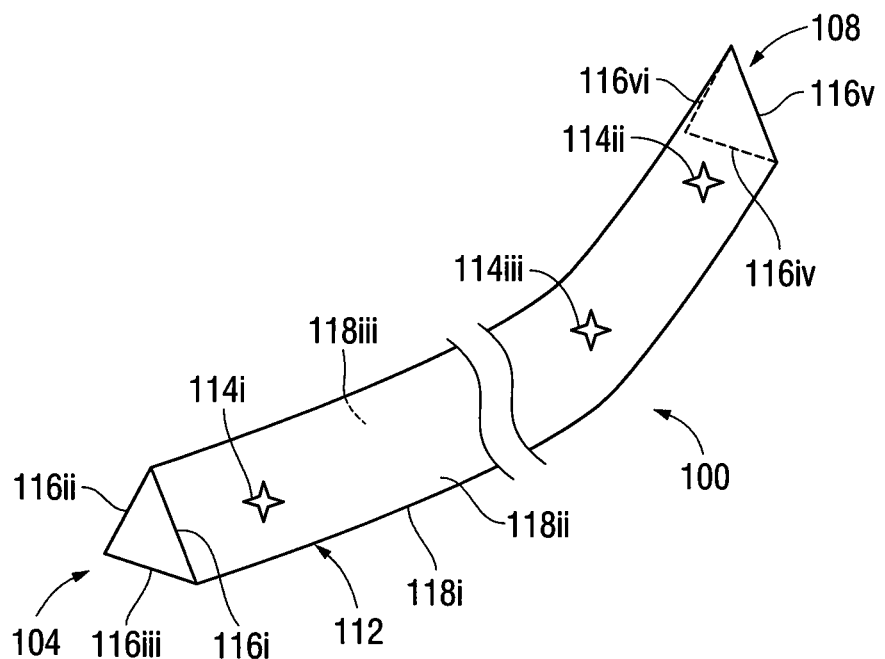
FIG. 5 is a (partial) perspective view of the primary delivery catheter including one or more markers (e.g., radiopaque markers) to facilitate external visualization of the primary delivery catheter in the blood vessel.

FIG. 5 provides a (partial) a (partial) view of the delivery catheter 100 rotated 120° (clockwise) from the orientation seen in FIG. 4 such that the face 118*ii* is visible. In the illustrated embodiment, the markers 114 are secured to (or otherwise supported on) the face 118*ii*. The markers 114 may be present in any suitable number and may be positioned in any suitable location. As such, it is envisioned that one or more markers 114 may be located on the face 118*i* or the face 118*iii* either instead of, or in addition to, the face 118*ii*. In the particular embodiment illustrated, for example, the delivery catheter 100 includes a (first) marker 114*i* located at (or adjacent to) the proximal end 104 of the delivery catheter 100 (e.g., on a hub of the delivery catheter 100 located externally of the body so as to allow for direct visualization), a (second) marker 114*ii* located at (or adjacent to) the distal end 108 of the delivery catheter 100, and a (third) marker 114*iii* located between the markers 114*i*, 114*ii*, wherein each of the markers 114 is oriented in a "12 o'clock" position.

Figure 6:
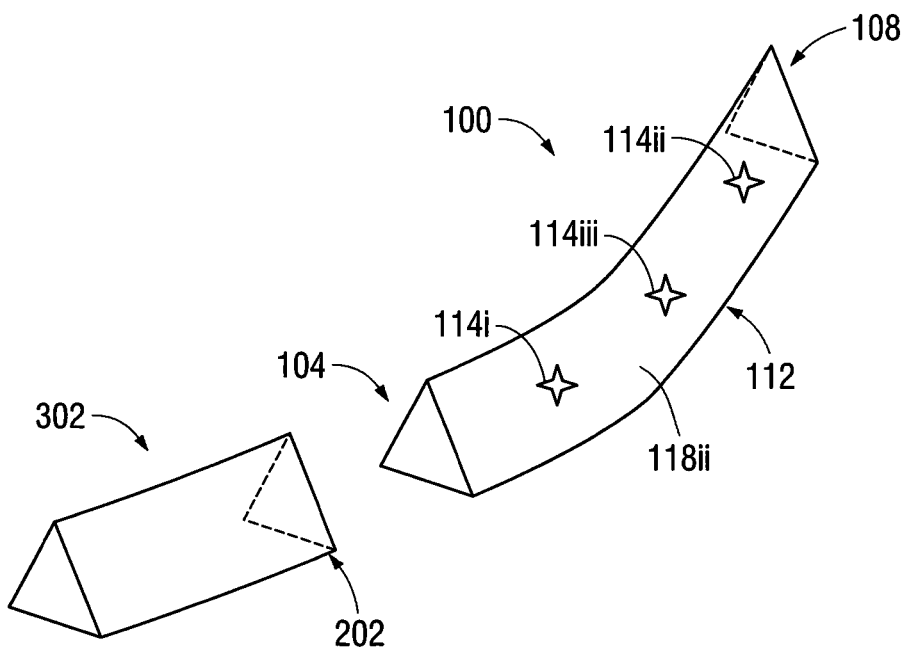
FIG. 6 is a perspective view of the pusher, the primary stent, and the primary delivery catheter seen in FIG. 5 illustrating insertion of the pusher and the primary stent into the primary delivery catheter.

FIG. 6 illustrates the stent 202 loaded onto the pusher 302 during insertion into the lumen 112 of the delivery catheter 100. As discussed above, the lumen 112 and the pusher 302 include corresponding non-circular (e.g., triangular) transverse cross-sectional configurations that inhibit (if not entirely prevent) relative rotation between the pusher 302 (and, thus, the stent 202) and the delivery catheter 100 while allowing for relative axial (longitudinal) movement (e.g., sliding) of the pusher 302 (and, thus, the stent 202) through the lumen 112.

As described below, however, a variety of other non-circular transverse (lateral) cross-sectional configurations are also contemplated by the present disclosure.

With reference to FIGS. 7A-7D, as indicated above, the lumen 112 extending through the delivery catheter 100 (as well as the pusher 302, the guide wire 500, the lumen 404 in the balloon catheter 400, etc.) may include a variety of non-circular transverse cross-sectional configurations such as, for example, a square-shaped configuration (FIG. 7A), a pentagonal configuration (FIG. 7B), an arrow-shaped configuration (FIG. 7C), a star-shaped configuration (FIG. 7D), or any other suitable non-circular transverse cross-sectional configuration that inhibits (if not entirely prevents) relative rotation between the pertinent structures. Note the lumens and outer diameters can correspond so they are the same configuration or can correspond so that although they are different configurations, they are non-circular and rotational movement is limited or fully inhibited.

FIG. 7E illustrates a variation on the delivery catheter 100 in which the proximal end 104 includes the markers 114*i*, 114*ii* in the "12 o'clock" position and the "6 o'clock" position, respectively, and the distal end 108 includes the marker 114*iii* in the "12 o'clock" position.

FIG. 8 shows the pusher 302.

FIG. 9 shows the packaging catheter 300 and the lumen 316 that extends through the elongated body 310 which, in the illustrated embodiment, includes a non-circular (e.g., triangular) transverse cross-sectional configuration.

Figure 10:
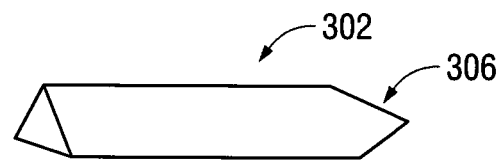
FIG. 10 is a perspective view of an alternate embodiment of the pusher, which includes a tapered distal end.

FIG. 10 illustrates an alternate embodiment of the pusher 302, wherein the distal end 306 includes a tapered configuration. It should be appreciated, however, that distal end 306 of the pusher 302 may include any suitable configuration in various embodiments of the present disclosure such as, for example, rounded, pointed, etc.

Figure 11:
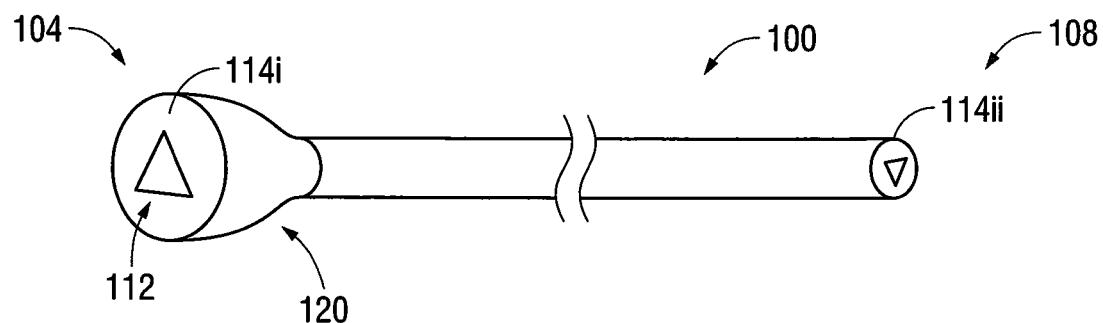
FIG. 11 illustrates an alternate embodiment of the primary delivery catheter, which includes a hub at a proximal end thereof and a series of markers (e.g., radiopaque markers).

FIG. 11 illustrates an embodiment of the delivery catheter 100 in which the proximal end 104 includes a hub 120. More specifically, the delivery catheter 100 is shown with the distal end 108 being (rotationally) offset from the proximal end 104 (e.g., subsequent to insertion into the blood vessel V (FIG. 2A)), as indicated by the markers 114*i*, 114*ii* respectively included at the proximal and distal ends 104, 108. In the particular orientation seen in FIG. 11, the delivery catheter 100 is deflected (twisted) such that the marker 114*ii* at the distal end 108 is in a "10 o'clock" position when compared to the "12 o'clock" position of the marker 114*i* at the proximal end 104, which is provided on the hub 120 (e.g., such that the distal end 108 of the delivery catheter 100 is (rotationally) offset from the proximal end 104 by (approximately) 60°).

Figure 12:
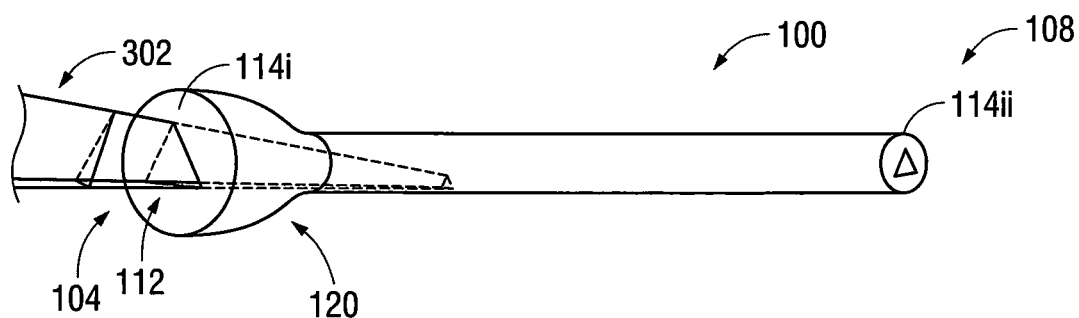
FIG. 12 illustrates the pusher inserted into the primary delivery catheter seen in FIG. 11.

FIG. 12 illustrates the pusher 302 inserted into the lumen 112 of the delivery catheter 100 seen in FIG. 11.

Figure 13:
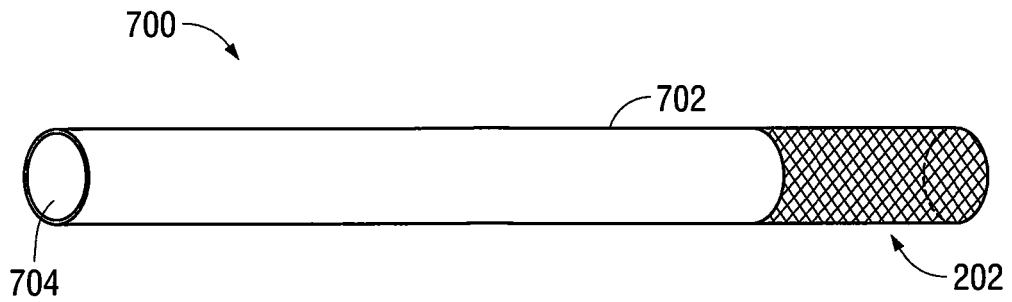
FIG. 13 is a perspective view of an alternate embodiment of the delivery device, which includes an outer hypotube that is configured to support the primary stent.
Figure 14:
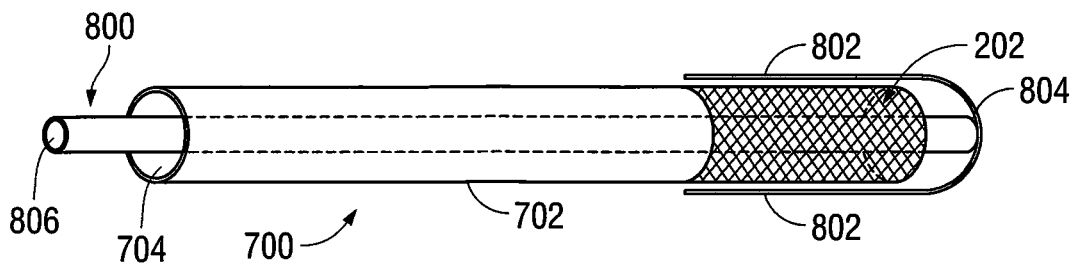
FIG. 14 is a perspective view of an inner hypotube inserted into the outer hypotube seen in FIG. 13.

FIGS. 13 and 14 illustrated an alternate embodiment of the disclosure in which the delivery device includes an elongated outer hypotube (member) 700 (FIG. 13) and an inner hypotube 800 (FIG. 14). The outer hypotube 700 supports the stent 202 (e.g., the stent 202 is secured or otherwise connected to) an outer surface 702 of the outer hypotube 700) and defines a lumen 704 that extends therethrough. While the outer hypotube 700 is illustrated as including a (generally) annular (circular, round) transverse cross-sectional configuration (e.g., for use during procedures in which rotation is not required), it should be appreciated that the outer hypotube 700 may include a non-circular transverse cross-sectional configuration in alternate embodiments (e.g., for use during procedures in which rotation is required).

The inner hypotube 800 includes wings 802 that extend proximally (rearwardly) from a distal end 804 thereof and defines a lumen 806 that extends therethrough. The inner hypotube 800 is configured for insertion into the lumen 704 of the outer hypotube 700 (FIG. 13) such that the wings 802 are positionable about the stent 202 to cover and constrain the stent 202 during insertion it the blood vessel V. During use of the hypotubes 700, 800, the stent 202 is exposed from the wings 802 by varying the relative longitudinal (axial) positions of the hypotubes 700, 800 (e.g. by moving the inner hypotube 800 proximally within the lumen 704 of the outer hypotube 700, by moving the outer hypotube 700 proximally in relation to the inner hypotube 800, etc.) to thereby unsheathe (expose) the stent 202, which allows the stent 202 to automatically expand within the blood vessel V. If necessary or desired (e.g., during movement or repositioning of the stent 202 within the blood vessel V), the stent 202 may be re-sheathed (covered) (e.g. by moving the inner hypotube 800 distally within the lumen 704 of the outer hypotube 700, by moving the outer hypotube 700 distally in relation to the inner hypotube 800, etc.).

It is envisioned that the lumen 806 extending through the inner hypotube 800 and/or the lumen 704 extending through the outer hypotube 700 may be configured to receive a guide wire (e.g., the aforementioned guide wire 500) to facilitate use in an "over-the-wire" method of deployment. It is also envisioned that the inner hypotube 800 and/or the outer hypotube 700 may include a rapid exchange configuration (e.g., it is envisioned that the inner hypotube 800 may include a side hole in communication with the lumen and/or that the outer hypotube 700 may include a side hole in communication with the lumen that is configured to receive the guide wire 500).

Figure 14A:
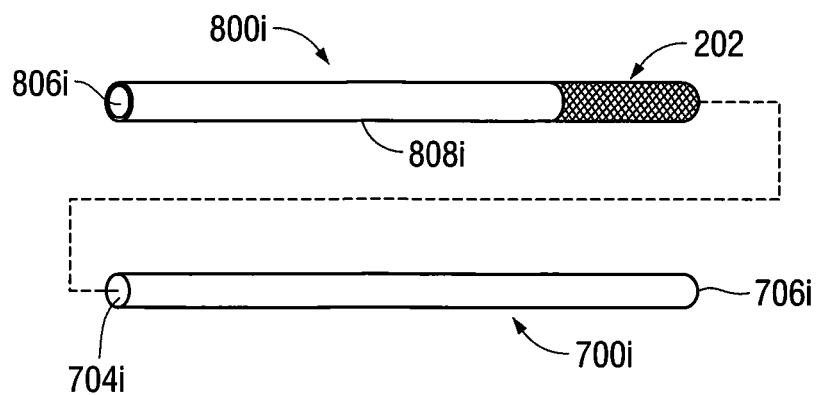
FIG. 14A is a perspective view of alternate embodiments of the outer hypotube and the inner hypotube.

FIG. 14A illustrates alternate embodiments of the outer and inner hypotubes 700, 800 seen in FIGS. 13 and 14, which are identified by the reference characters 700*i* and 800*i*, respectively, for use during an alternate procedure. The inner hypotube 800*i* includes a lumen 806*i* that extends therethrough and supports the stent 202, which is loaded (connected, supported) to an outer surface 808*i* thereof. The outer hypotube 700*i* includes a lumen 704*i* that is configured to receive the inner hypotube 800*i* such that the inner hypotube 800*i* is longitudinally (axially) movable through the outer hypotube 700*i*. Upon sufficient relative longitudinal (axial) movement between the hypotubes 700*i*, 800*i*, the stent 202 is exposed from a distal end 706*i* of the outer hypotube 700*i* and is automatically deployed (expanded).

Figure 15:
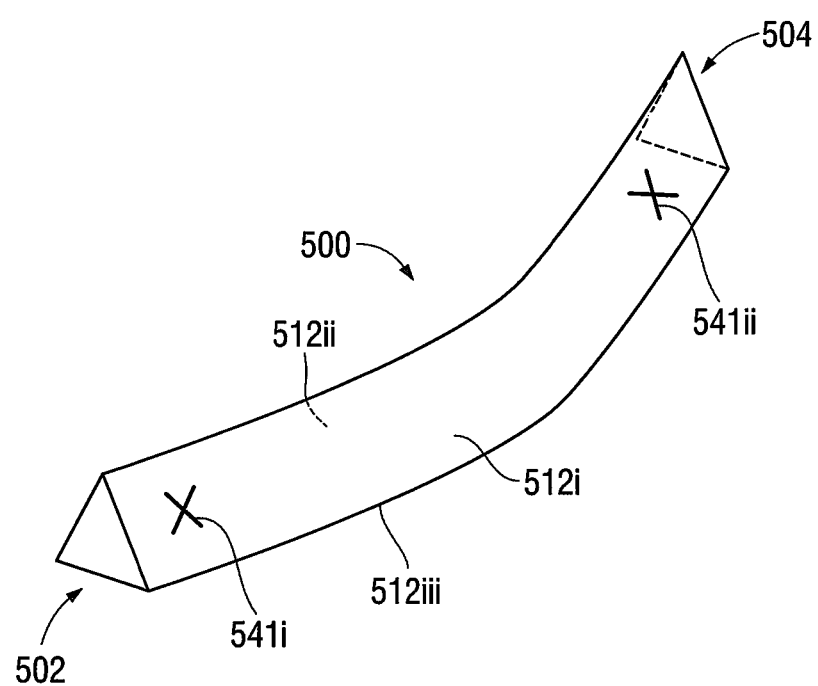
FIG. 15 is a perspective view of a guide wire for use with the presently disclosed intravascular system.
Figure 22:
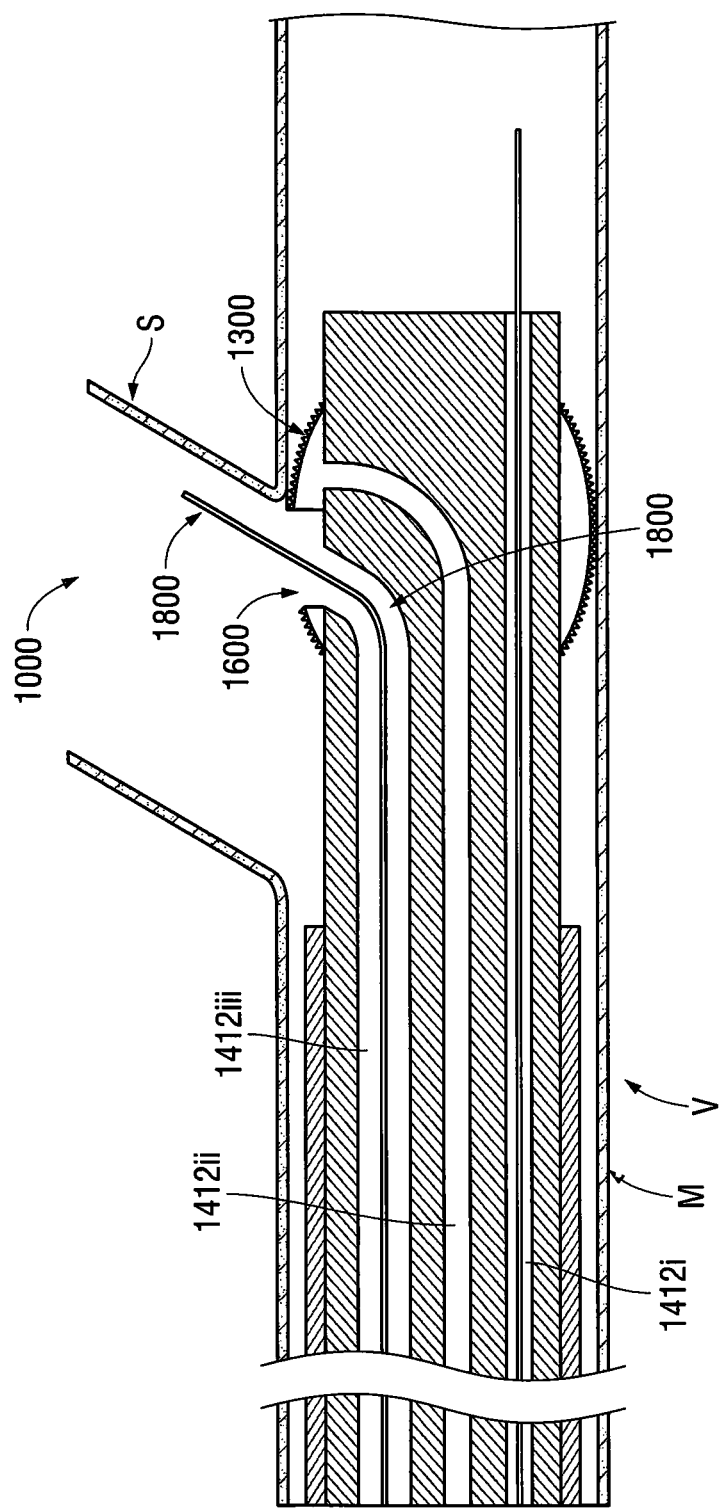
FIG. 22 is a longitudinal, cross-sectional view illustrating deployment of a secondary guide wire through the primary delivery catheter and the first delivery device into the side branch of the blood vessel.

FIG. 15 illustrates the guide wire 500. In the illustrated embodiment, the guide wire 500 includes a non-circular (e.g., triangular) transverse cross-sectional configuration that defines three linear faces (sides), which are identified by the reference characters 512*i*, 512*ii*, 512*iii*. Although shown as being (generally) triangular in configuration, it should be appreciated that alternative embodiments (not shown) may employ other non-circular cross-sectional configurations, such as, for example, rectangles, pentagons, hexagons, octagons, squares, ovals, stars, arrows, etc. In the configuration seen in FIG. 15, the guide wire 500 is illustrated without any significant (rotational) offset between the respective proximal and distal ends 502, 504 thereof.

DETAILED DESCRIPTION OF THE INVENTION

The embodiments of the device and variants of the device of the present disclosure are set forth with reference to the above drawings.

Referring to FIG. 1A, the delivery catheter 100 is illustrated. As discussed above, the aforementioned lumen 112 extends through the delivery catheter 100 and includes a (first) non-circular transverse (lateral) cross-sectional configuration. Although the transverse (lateral) cross-sectional configuration of the lumen 112 is shown as being (generally) triangular in FIG. 1A, a variety of other non-circular transverse (lateral) cross-sectional configurations are also contemplated by the present disclosure including, for example, rectangular, pentagonal, hexagonal, octagonal, square-shaped, ovate (elliptical), stars-shaped, arrow-shaped, etc., as mentioned above. The lumen 112 is configured to (slidably) receive an (elongated) medical device, such as, for example, the pusher 302 (FIG. 2A) of the packaging catheter 300, the balloon catheter 400 (FIG. 2B), the hypotube 700 (FIG. 13), the hypotube 800 (FIG. 14), the hypotube 700*i* (FIG. 14A), the hypotube 800*i* (FIG. 14A), the guide wire 500, etc. As described in further detail herein, it is envisioned that the medical device intended for insertion into the lumen 112 may include a (second) non-circular transverse (lateral) cross-sectional configuration corresponding to the (first) non-circular transverse (lateral) cross-sectional configuration defined by the lumen 112 so as to allow for longitudinal (axial) movement (e.g., sliding) of the medical device through the delivery catheter 100 while inhibiting (if not entirely preventing) rotation of the medical device within the delivery catheter 100 to thereby facilitate control over the (rotational) orientation of the medical device during deployment and placement of the stent 202. Depending upon the particular geometry of the transverse cross-sectional configurations defined by the lumen 112 and the medical device, the medical device will be insertable into the lumen 112 in a certain number of discrete (rotational) orientations. For example, in the context of the triangular transverse cross-sectional configuration seen in FIG. 1A, an inserted medical device will be orientable in one of three distinct (rotational) orientations that are offset from each other by (approximately) 120°. Depending upon the particular transverse cross-sectional configuration employed, however, it should be appreciated that the number of distinct (rotational) orientations, and the offset therebetween, may be varied. For example, in the context of a square-shaped transverse cross-sectional configuration, an inserted medical device will be orientable in one of four distinct (rotational) orientations that are offset from each other by (approximately) 90°.

FIG. 1B illustrates the delivery catheter 100 within the blood vessel V. For simplicity and clarity, only the lumen 112 is illustrated. The delivery catheter 100 is positioned within the blood vessel V such that the distal end hole 110 is located in proximity (e.g., at or adjacent) to the aneurysm A (or other vascular abnormality) that is the subject of the associated medical procedure. Due to the generally linear configuration and geometry of the lumen 1, the delivery catheter 100 includes a set orientation in which one side is positioned closest to the target aneurysm A.

FIG. 1C illustrates the pusher 302 positioned with the lumen 112 of the delivery catheter 100 in a first orientation and FIG. 1D illustrates the pusher 302 and the delivery catheter 100 in a second, different orientation that is rotationally offset from the first orientation. More specifically, FIG. 1D illustrates the pusher 302 and the delivery catheter 100 after 120° of counterclockwise rotation (or 240° of clockwise rotation). Rotation of the delivery catheter 100 and, thus, the pusher 302, allows for the delivery and placement of the occlusion device 200 (e.g., the stent 202) (FIGS. 2A, 2C) in a necessary or desired orientation dictated by the location of the aneurysm A, for example. A similar setup may be used to deliver other devices, such as aneurysm neck caps which may have an asymmetric shape to cover an asymmetric aneurysm neck, previously described by Walzman (U.S. Pat. No. 10,543,015). It is envisioned that one or more supplemental (additional) occlusion device(s) 200 may be used as well during the course of a particular medical procedure. As described herein, the orientation of the medical device (e.g., the pusher 302 and the stent 202) inserted through the delivery catheter 100 may be fixed outside the patient's body by fixing the orientation of the medical device relative to the delivery catheter 100. The orientation of the delivery catheter 100 (e.g. relative to the aneurysm A) may be established prior to insertion of the medical device into the lumen 112 such as, for example, via imaging, so as to facilitate proper insertion of the medical device to achieve proper orientation and placement of the stent 202 with respect to aneurysm A without necessitating any rotational manipulation (e.g., turning) of the pusher 302 and, thus, the stent 202, inside the patient.

FIG. 2A illustrates the packaging catheter 300 connected to the delivery catheter 100 via the hub 600 such that the elongated body 310 is positioned externally of the patient. In the illustrated embodiment, the lumen 316 extending through the elongated body 310 of the packaging catheter 300 includes a non-circular transverse (lateral) cross-sectional configuration corresponding to that defined by the lumen 112 of the delivery catheter 100 and that defined by the pusher 302. Although shown as being (generally) triangular in FIG. 2A, it should be appreciated that the transverse cross-sectional configuration defined by the lumen 316 of the elongated body 310 of the packaging catheter 300 may be varied in alternate embodiments without departing from the scope of the present disclosure (e.g., depending upon the particular transverse cross-sectional configurations defined by the lumen 112 of the delivery catheter 100 and the pusher 302).

The distal end 306 of the pusher 302 (releasably) supports the stent 202 such that the stent 202 is positionable in proximity (e.g., at or adjacent) to the aneurysm A. Insertion of the pusher 302 and the stent 202 into the lumen 112 of the delivery catheter 100 is facilitated via positioning of the distal end 20 of the packaging catheter 300 and the proximal end 104 of the delivery catheter 100 within the hub 600. To facilitate proper relative orientation of the packaging catheter 300 (e.g., the pusher 302 and the stent 202) and the delivery catheter 100, as well as proper orientation of the packaging catheter 300 within the blood vessel V, in the illustrated embodiment, the hub 600 include one or more markers (e.g., radiopaque markers) 604 and the packaging catheter 300 includes one or more markers (e.g., radiopaque markers) 318 (e.g., respective (first and second) markers 318*i*, 318*ii* that are positioned at (or adjacent to) the proximal and distal ends 304, 306 of the elongated body 310) which can be aligned with the marker(s) 114 FIG. 5 on the delivery catheter 100. The marker(s) 604 on the hub 600, the marker(s) 318 on the packaging catheter 300, and the marker(s) 114 on the delivery catheter 100 are located in corresponding (rotational) positions, which allows the relative orientations of the packaging catheter 300, the hub 600, and the delivery catheter 100 to be ascertained and controlled (e.g., via rotation of the elongated body 310 of the packaging catheter 300, the pusher 302, and/or the delivery catheter 100). In the illustrated embodiment, for example, the marker(s) 604 on the hub 600, the marker(s) 318 on the packaging catheter 300, and the marker(s) 114 on the delivery catheter 100 are each shown in the "12 o'clock" position. It should be appreciated, however, that the marker(s) 604, 318, and 114 may be located in any position suitable for the intended purpose of facilitating proper relative (rotational) orientation of the packaging catheter 300 (e.g., the pusher 302 and the stent 202) and the delivery catheter 100.

In the particular embodiment of the disclosure seen in FIG. 2A, during use, the packaging catheter 300 is connected to the hub 600 such that the marker 604 on the hub 600 is oriented in the "12 o'clock" position. Based upon the particular configuration of the stent 202, when so positioned, the pusher 302 and the stent 202 may be oriented in a predetermined fashion (e.g., such that the first region 204 (or the second region 206) of the stent 202 faces (or is otherwise (rotationally) aligned with) the aneurysm A.

FIG. 3 illustrates positioning of the pusher 302 and the stent 202 within the blood vessel V following removal of the delivery catheter 100 (FIG. 2A). Once the stent 202 is located in proximity (e.g., at or adjacent) to the aneurysm A, the stent 202 may be activated, released, or otherwise deployed such that the stent 202 expands within the blood vessel V. For example, when configured as a self-expanding stent, the stent 202 will automatically expand upon the removal of an external constraint (e.g., such as that provided by the delivery catheter 100). Alternatively, however, it is envisioned that the stent 202 may be deployed via the balloon catheter 400 (FIG. 2B) upon inflation of the inflatable member 406.

In the particular embodiment illustrated, for example, the stent 202 is oriented such that the first (covered, less porous) region 204 abuts the aneurysm A while the second (uncovered, more porous) region 206 of the stent 202 promotes (or otherwise permits) blood flow to any side branches of the blood vessel V the stent 202 may cross. Although it is envisioned that the stent 202 may include a (generally) cylindrical configuration upon expansion, as seen in FIG. 2C, for example, it is envisioned that the configuration of the stent 202 may varied in alternate embodiments of the disclosure (e.g., depending upon the particular requirements of the surgical procedure, the configuration and/or orientation of the aneurysm A (or other vascular abnormality), etc.). It is also envisioned that the stent 202 may be (temporarily) crimped (or otherwise deformed) into an alternate shape when loaded onto the pusher 302, the inflatable member 406 of the balloon catheter 400, or other such suitable medical device. It should be appreciated, however, that the configuration of the medical device supporting the stent 202 may be altered or varied as necessary or desired to facilitate placement of the stent 202 in the intended manner. For example, it is envisioned that the medical device supporting the stent 202 may include a cylindrical or non-cylindrical configuration in various locations along the length thereof (e.g., proximally of the stent 202, distally of the stent 202, and/or within the stent 202). When being crimped on a (round, circular, tubular, toroidal) inflatable member 406, for example, it is envisioned that inflatable member 406 may be collapsed, deflated, and mounted on an elongate member, such as, for example, the body 402 of the balloon catheter 400, having a suitable configuration such that the inflatable member 406 (when deflated) and the stent 202 (when collapsed) may assume corresponding (e.g., similar or identical) configurations. It is envisioned that an external crimper of the same configuration may be used during the crimping process.

Now referring to FIG. 4, the lumen 112 of the delivery catheter 100 is illustrated. More specifically, FIG. 4 illustrates the delivery catheter 100 devoid of any (rotational) offset between the distal end 108 and the proximal end 104. It is envisioned that the (generally) triangular (transverse) cross-sectional configuration of the lumen 112 may promote (or otherwise facilitate) identification of the (rotational) orientation of the lumen 112.

FIG. 5 illustrates the delivery catheter 100 rotated (approximately) 120° (clockwise) from the orientation seen in FIG. 4 such that the linear face 555 is visible. In the particular embodiment shown, the linear side 555 includes the marker(s) 114, which promote visualization and proper orientation of the delivery catheter 100 during placement within the blood vessel V by allowing the clinician to ascertain the orientation of the linear face 555 relative to any suitable component of the intravascular system 10 or anatomical structure (e.g., the aneurysm A). Using that information, it is envisioned that the packaging catheter 300 may be properly oriented (e.g., relative to the hub 600) such that, upon advancement of the pusher 302 and the stent 202 through the delivery catheter 100, the stent 202 may be oriented as necessary or desired (e.g., such that the first (covered, less porous) region 204 of the stent 202 abuts the aneurysm A).

In certain embodiments, it is envisioned that the marker 114*ii* at the distal end 108 of the delivery catheter 100 may to (further) support visualization of the (rotational) position of the distal end 108 of the delivery catheter 100 (e.g., relative to the aneurysm A, a lesion, a side branch of the blood vessel V, or other such anatomical structures).

FIG. 6 illustrates the stent 202 supported on the pusher 302 prior to insertion of the stent 202 and the pusher 302 into the lumen 112 of the delivery catheter 100. During introduction into the blood vessel V, by virtue of the stent 202 being crimped (or otherwise secured to the pusher 302), the stent 202 is in a first (initial, insertion) configuration in which the stent 202 includes a transverse cross-sectional configuration corresponding to that defined by the pusher 302. Thus, in the illustrated embodiment, the stent 202 includes a (generally) triangular transverse cross-sectional configuration prior to deployment. Upon expansion, however, the stent 202 moves into a second (subsequent, active) configuration in which the stent 202 includes a transverse cross-sectional configuration that may differ from that defined by the stent 202 in the first configuration. For example, in the particular embodiment illustrated, upon deployment (exposure) of the stent 202 from the distal end 108 of the delivery catheter 100 (within the blood vessel V) and removal of the constraint provided by the delivery catheter 100, the stent 202 automatically expands into the (generally) cylindrical (tubular) configuration seen in FIG. 2C.

First Method

In one method of use, the delivery catheter 100 is inserted into the blood vessel V with the proximal end 104 thereof positioned at or adjacent to the hub 600 and the markers 114*i*, 114*ii* in the "12 o'clock" position, which allows the degree of (rotational) deflection experienced by the delivery catheter 100 during insertion into the blood vessel V (if any) to be ascertained (e.g., via external visualization using any suitable technique). The packaging catheter 300, which includes the pusher 302 and the stent 202, is then inserted into the delivery catheter 100. In the particular method described, the stent 202 includes the differential porosity described above, which is attributable to the disparity between the regions 204, 206 (FIG. 2C). After ascertaining the degree of (rotational) deflection experienced by the distal end 108 of the delivery catheter 100 (if any) (e.g., relative to the hub 600), the packaging catheter 300 is oriented accordingly to reduce (if not entirely eliminate) any (rotational) offset between the stent 202 and the distal end 108 of the delivery catheter 100.

As mentioned above, it is envisioned that the hub 600 and the packaging catheter 300 may include one or more markers 604, 318, respectively, to support more precise relative (rotational) orientation between the packaging catheter 300 and the delivery catheter 100. The markers 604, 318 may be disposed in any position to point to any direction. The term "12 o'clock" should be not construed as limiting in any way, but rather, as an exemplary indicator of position. For example, the clinician (user) may be instructed to rotate the hub 600 to a "3 o'clock" position, to a "6 o'clock" position, to a "9 o'clock" position, etc., which intuitively suggests a quarter-turn, a half-turn, a three-quarter turn, etc., respectively, with other "times" referring to approximate positions therebetween (e.g., a "2 o'clock" position, a "5 o'clock" position, an "11 o'clock" position, etc.). The same effect could be achieved by reference to a "North" marker, utilizing terminology such as "East," "South," and "West" (or interstitial positions such as "ESE" or "NW"). The delivery catheter 100 and the packaging catheter 300 may be configured for rotation through a 360° range of motion (e.g., prior association (engagement, connection) with one another) to allow for positioning of the delivery catheter 100 and the packaging catheter 300 in any manner desired or necessitated by the particular procedure being conducted (e.g., based upon the size, location, nature, etc., of the vascular abnormality being treated).

Following connection of the packaging catheter 300 and the delivery catheter 100 (e.g., via mutual connection to the hub 600), the stent 202 is inserted into the delivery catheter 100 at a particular orientation (e.g., relative to the "12 o'clock" marker(s) 114 on the delivery catheter 100). After insertion into the delivery catheter 100, the final (rotational) orientation of the stent 202 will be dictated by (and will correspond to) the (rotational) orientation of the distal end 108 of the delivery catheter 100. For example, even if it introduced in the "12 o'clock" position at the hub 600, the stent 202 may be deployed in the "3 o'clock" position, the "6 o'clock" position, etc., depending upon the degree of (rotational) deflection experienced by the delivery catheter 100 during navigation of the blood vessel V en route to the aneurysm A (for example), if any, which is identifiable via the marker 114*ii* located at the distal end 108 thereof.

If the predicted (rotational) position of the stent 202 is not suitable (e.g., if a different (rotational) position for the stent 202 is necessary or desired), the stent 202 may be rotated accordingly (e.g., relative to the marker 114*ii* at the distal end 108 of the delivery catheter 100) prior to insertion into the delivery catheter 100 (e.g., via rotational manipulation of the packaging catheter 300 (e.g., the pusher 302)). Additionally, or alternatively, it is envisioned that the final the (rotational) position of the stent 202 may be varied via rotational manipulation of the delivery catheter 100 and, thus, the pusher 302 and the stent 202, following insertion of the pusher 302 and the stent 202 into the delivery catheter (e.g., the delivery catheter, the pusher 302, and the stent 202 may be rotated in unison via the non-rotational interface provided by the corresponding non-circular (transverse) cross-sectional configurations defined by the pusher 302 and the lumen 112 extending through the delivery catheter 100).

In the context of triangular (transverse) cross-sectional configurations for the pusher 302 and the lumen 112, the packaging catheter 300 may be positioned in three discrete (rotational) positions prior to insertion of the pusher 302 into the lumen 112 of the delivery catheter 100. To facilitate additional (rotational) precision, it is envisioned that the stent 202 may be pre-loaded into the elongated body 310 of the packaging catheter 300 in a variety of (rotational) orientations (e.g., during packaging by the manufacturer), which may be identified via labeling on the device, its packaging, etc.

The process may be repeated to verify that the respective markers 114, 318 on the delivery catheter 100 and the packaging catheter 300 are consistently aligned. Imaging may then be performed to verify the relative (rotational) positions of the markers 114, 318 to determine the (rotational) orientation (e.g., the "hour" on the "clock") required of the stent 202 (prior to insertion into the delivery catheter 100) to achieve the necessary final (rotational) position within the blood vessel V.

In certain embodiments, prior to insertion of the stent 202, the final (rotational) position of the stent 202 may be confirmed via the insertion of a test stent (or other such device), which may be temporarily advanced in the predicted orientation, visualized using any suitable imaging technique, and then removed prior to insertion and deployment of the stent 202. To facilitate such visualization, it is envisioned that the test stent (or other such device) may include one or more suitable markers (e.g., radiopaque markers). For example, during a test insertion, in the instance where a fenestration is identified at the "7 o'clock" position (which is offset by (approximately) 90° in the clockwise direction relative to the target branch vessel), the packaging catheter 300 may be re-oriented into the "4 o'clock" position to facilitate proper orientation of the stent 202.

Upon imaging of the distal end 108 of the delivery catheter 100, and confirmation that the distal end 108 is positioned as necessary, the stent 202 may be loaded into the delivery catheter 100 in the appropriate (necessary) orientation and advanced to the target site.

Second Method

A second method of use will now be discussed, which uses the steps, devices, markers, etc., discussed above in connection with the First Method. As mentioned above, the lumen 112 extending through the delivery catheter 100 includes a unique (transverse), non-circular cross-sectional configuration while, in an exemplary embodiment, the delivery catheter 100 includes an outer (transverse) cross-sectional configuration that is (generally) annular (e.g., round, circular) to facilitate advancement of the delivery catheter 100 through a patient's vasculature, circulatory vessels, etc. The non-circular (transverse) cross-sectional configuration defined by the lumen 112 reduces (if not eliminates) relative rotation between the delivery catheter 100 and an inserted medical device (e.g., the pusher 302, the hypotube 700 (FIG. 13), the hypotube 800 (FIGS. 13, 14), the balloon catheter 400, etc.) to improve precision during placement within the blood vessel V to enhance predictability in the final position of the stent 202.

While the lumen 112 is (generally) illustrated as including a triangular (transverse) cross-sectional configuration, alternative configurations are also contemplated herein (e.g., square, hexagonal, octagonal, pentagonal, a "house" silhouette, oval, elliptical, star-shaped, etc.). In the context of a star-shaped (transverse) cross-sectional configuration, any style of star may be used including, for example, a six-pointed star, a "Star of David," etc.

It is envisioned that the (transverse) cross-sectional configuration of the lumen 316 extending through the elongated body 310 of the packaging catheter 300 may correspond to that of the lumen 112 extending through the delivery catheter 100, as can be appreciated through reference to FIGS. 1A-2A, for example. The interface defined by the lumen 316 and the medical device positioned therein (e.g., the pusher 302, the hypotube 700 (FIG. 13), the hypotube 800 (FIGS. 13, 14), etc.) is such that the lumen 316 permits longitudinal (axial) movement (e.g., sliding) of the medical device therethrough while inhibiting (if not entirely preventing) relative rotation between the medical device within the lumen 316 and the packaging catheter 300, which allows the (rotational) position of the medical device relative to the packaging catheter 300 (and the delivery catheter 100) to be (substantially) maintained, thereby facilitating accurate and predicable deployment (e.g., of the stent 202).

In another example, the aforementioned guide wire 500 may be utilized to facilitate deployment of the stent 202 via the balloon catheter 400, as seen in FIG. 2B. In such implementations, the guide wire 500 may be advanced into the blood vessel V via any suitable endovascular method. To inhibit (if not entirely prevent) relative rotation between the balloon catheter 400 and the guide wire 500 and thereby facilitate control over the (rotational) orientation of the balloon catheter 400 and the stent 202, it is envisioned that the guide wire 500 and the lumen 404 extending through the elongated body 402 of the balloon catheter 400 may include corresponding non-circular (e.g., triangular) (transverse) cross-sectional configurations. In various embodiments, it is envisioned that the non-circular (transverse) cross-sectional configuration may extend continuously along an entire length of the guide wire 500. Alternatively, it is envisioned that the non-circular (transverse) cross-sectional configuration may only extend along a portion of the length of the guide wire 500.

To facilitate visualization of the guide wire 500 in vivo, the guide wire 500 may include one or more markers 514 (e.g., radiopaque or other such markers). For example, in the particular embodiment seen in FIG. 2B, the guide wire 500 includes a first marker 514*i* located at (or adjacent to) the proximal end 502 of the guide wire 500 (which may be located externally of the patient) and a second marker 514*ii* located at (or adjacent to) the distal end 504 of the guide wire 500), each of which may be located in the "12 o'clock" position (or any other suitable reference orientation). In one particular embodiment, it is envisioned that the marker(s) 514 may be located at (or adjacent to) a transition between a first portion of the guide wire 500, which includes the non-circular (transverse) cross-sectional configuration, and a second portion of the guide wire 500, which includes a (generally) circular (transverse) cross-sectional configuration. It is also envisioned, however, that a variety of distinct radiopaque markers 514, such as those of a different radiodensity, shape or orientation, etc., may be utilized (e.g., to further facilitate visualization, differentiation, etc.) in connection with the guide wire 500 (or any of the components of the intravascular system 10 described herein including, for example, the delivery catheter 100, etc.). Via visualization, the (rotational) position of the marker 514*ii* can be determined relative to the marker 514*i*, the any vascular abnormalities (e.g., the aneurysm A), the origin of a side branch, etc.

Once the (rotational) position of the marker 514*ii* at the distal end 504 of the guide wire 500 is determined, the balloon catheter 400 may be advanced into the blood vessel V over the guide wire 500 such that the guide wire 500 is received within the lumen 404.

Following positioning of the balloon catheter 400 within the blood vessel V as desired, the inflatable member 406 can be expanded to thereby deploy (implant) the stent 202. As indicated above, if desired, a test stent (or other such device) may be deployed and recaptured prior to placement of the stent 202 to confirm the rotational position of the guide wire 500 and, thus, the predicted final position of the stent 202, at the target location (e.g., at or adjacent to the aneurysm A).

In various alternate embodiments, it is envisioned that the guide wire 500 and the balloon catheter 400 may be configured (adapted) for use in both "over-the-wire" configurations, as discussed above, and rapid-exchange configurations.

In another exemplary procedure, it is envisioned that the guide wire 500 may be used in combination with the packaging catheter 300 to facilitate placement and deployment of the pusher 302 and the stent 202 through the delivery catheter 100. In such embodiments, the guide wire 500 may be utilized to facilitate the placement of the delivery catheter 100 into the blood vessel V over the guide wire 500. In such embodiments, it is envisioned that the guide wire 500 and the lumen 112 (FIG. 1A) extending through the delivery catheter 100 may include corresponding non-circular (transverse) cross-sectional configurations to inhibit (if not entirely prevent) relative rotation between the delivery catheter 100 and the guide wire 500.

Following placement of the guide wire 500 and insertion of the delivery catheter 100 into the blood vessel V over the guide wire 500, the guide wire 500 may be removed, thereby allowing for insertion of the pusher 302 and the stent 202 into to delivery catheter 100 from the elongated body 310 of the packaging catheter 300. As indicated above, it is also envisioned that the pusher 302 and the lumen 112 extending through the delivery catheter 100 may include corresponding non-circular (transverse) cross-sectional configurations. Thus, in such embodiments, the (transverse) cross-sectional configuration defined by the lumen 112 extending through the delivery catheter 100 may be common to (shared by) both the pusher 302 and the guide wire 500.

In such embodiments, upon sufficient advancement of the pusher 302 through the delivery catheter 100, the stent 202 emerges from the distal end thereof, at which point, the external constraint applied to the stent 202 by the lumen 112 is removed such that the stent 202 is automatically deployed in the blood vessel V.

To facilitate the delivery of the (self-expanding) stent 202, during the course of an "over-the-wire" procedure, it is envisioned that inner and outer hypotubes (e.g., catheters) may be utilized in place of the pusher 302. In the embodiment of the disclosure seen in FIGS. 13 and 14, for example, the stent 202 is loaded (mounted) on the outer hypotube 700. The inner hypotube 800 is positioned over the guide wire 500 (e.g., such that the guide wire 500 extends through the lumen 9094) and is received by the lumen 704 of the outer hypotube 700. It is envisioned that the lumen 9094 and the guide wire 500 may include corresponding non-circular (transverse) cross-sectional configurations, which, as discussed above, allows for relative axial movement between the guide wire 500 and the inner hypotube 800 while inhibiting (if not entirely preventing) relative rotation between the guide wire 500 and the inner hypotube 800. The wings 802 extend from the inner hypotube 800 in the proximal direction so as to cover (sheath) the stent 202 during insertion into the blood vessel V, thereby constraining the stent 202 so as to maintain the stent 202 in a collapsed configuration during insertion into the blood vessel V. Once the stent 202 is positioned as desired within the blood vessel V (e.g., in proximity (at or adjacent) to the aneurysm A), the relative longitudinal (axial) positions of the hypotubes 9091, 9092 can be varied to cause unsheathing of the stent 202

(e.g., exposure from the wings 802) so as to remove the external constraint provided by the wings 802 and permit expansion (deployment) of the stent 202.

In an alternate embodiment, which is illustrated in FIGS. 13A and 14A, the stent 202 is supported on an inner hypotube 800*i*, which extends into an outer hypotube 700*i* such that the outer hypotube 700*i* overlies the stent 202 to thereby constrain the stent 202 and inhibit expansion thereof during insertion into the blood vessel V. In such embodiments, the inner hypotube 800*i* is inserted over the guide wire 500 (e.g., such that the guide wire 500 is received within a lumen 9094*i* of the inner hypotube 800*i*). As discussed in connection with the hypotubes 9091, 9092, it is envisioned that the lumen 9094*i* and the guide wire 500 may include corresponding (transverse) cross-sectional configurations to inhibit (if not entirely prevent) relative rotation between the guide wire 500 and the inner hypotube 800*i* while allowing for relative axial movement between the guide wire 500 and the inner hypotube 800*i*. Once the stent 202 is positioned as desired within the blood vessel V (e.g., in proximity (at or adjacent) to the aneurysm A), the outer hypotube 700*i* can be retracted (moved in the proximal direction), thereby exposing the stent 202 and removing the external constraint provided by the outer hypotube 700*i* to permit expansion (deployment) of the stent 202.

In various embodiments of the disclosure, it is envisioned that the medical devices described herein may include an energy component 900 (FIG. 2C) that is configured to deliver ultrasound, RF energy, etc., to the target site (e.g., the aneurysm A). It can be delivered through the stent or adjacent the stent. For example, it is envisioned that the delivery of energy to the target site may soften calcifications in the walls of the blood vessel V (e.g., in the context of an intravascular lithotripsy, similar to those devices produced by Shockwave Medical).

Although shown as being associated with the stent 202 (FIG. 2C), it should be appreciated that the energy component 900 may be associated with any of the medical devices (or components thereof) described herein and that energy may be delivered in any suitable manner using any suitable structure(s) (e.g., wire(s), etc.). For example, it is envisioned that the energy component 900 may be provided on (or otherwise in communication with) the delivery catheter 100, the balloon catheter 400 (e.g., the inflatable member 406), the guide wire 500, the pusher 302, the anchor(s) 506, etc.

In another embodiment of the disclosure, the devices and methods described herein may be adapted for the treatment of bifurcated vessels, lesions, etc. With reference to FIGS. 16 and 17, an alternate embodiment of the intravascular system 10 is disclosed, which is identified by the reference character 1000. The intravascular system 1000 includes a primary delivery catheter 1100 defining a lumen 1102 and a (first) delivery device 1200 that is configured for insertion into the blood vessel V through the delivery catheter 1100 to deploy a primary stent 1300 (e.g., a first fenestrated occlusion device), which may be substantially similar or identical to the aforedescribed stent 202.

In the embodiment seen in FIG. 17, the (first) delivery device 1200 is configured as the aforedescribed packaging catheter 300 (FIG. 2A). In such embodiments, the primary stent 1300 is carried (supported) on the pusher 302 and is configured for self-expansion upon exposure from the delivery catheter 1100. To inhibit relative rotation between the delivery catheter 1100 and the primary stent 1300, it is envisioned that the lumen 1102 of the delivery catheter 1100 and the pusher 302 may include corresponding non-circular (e.g., triangular) (transverse) cross-sectional configurations.

Alternatively, with reference to FIGS. 18-25, it is envisioned that the (first) delivery device 1200 may be configured as a balloon catheter 1400. The balloon catheter 1400 includes an elongated body (member) 1402 with proximal and distal ends 1404, 1406 respectively defining end holes 1408, 1410 and a series of lumens 1412 that extend therethrough. More specifically, the balloon catheter 1400 includes a (first) lumen 1412*i*, a (second) lumen 1412*ii* that extends in (generally) parallel relation to the lumen 1412*i*, and a (third) lumen 1412*iii* that extends in (generally) parallel relation to the lumen 1412*i* and/or the lumen 1412*ii*. The balloon catheter 1400 further includes an inflatable member (balloon) 1414 that is secured to the elongated body 1402 and supports the primary stent 1300. In the particular embodiment illustrated, the inflatable member 406 includes a (first) fenestration (opening, aperture) 1416 and the primary stent 1300 includes a (second) fenestration (opening, aperture) 1302.

In certain embodiments, it is envisioned that the lumen 1412*i* may extend between the respective proximal and distal end holes 1408, 1410 of the balloon catheter 1400. Alternatively, the lumen 1412*i* may extend along only a portion of the length of the balloon catheter 1400 (e.g., from a (first, proximal) side hole to the distal end hole 1410) to support rapid-exchange of the balloon catheter 1400. The lumen 1412*i* is configured to receive a primary (first) guide wire 1500, which may be substantially similar or identical to the aforedescribed guide wire 500. As discussed above in connection with other embodiments of the disclosure, the lumen 1412*i* and the primary guide wire 1500 may include corresponding non-circular (transverse) cross-sectional configurations so as to allow for relative axial movement between the primary guide wire 1500 and the balloon catheter 1400 while inhibiting (if not entirely preventing) relative rotation between the primary guide wire 1500 and the balloon catheter 1400 to facilitate control over the (rotational) orientation of the balloon catheter 1400 and, thus, the primary stent 1300. In such "over-the wire" configuration, it is envisioned that there may be a third branch outside the patient's body that constitutes a proximal extension of the lumen 1412*i*.

The lumen 1412*ii* is configured to communicate fluid from a source of inflation to the inflatable member 1414. In the particular embodiment illustrated, it is envisioned that the lumen 1412*ii* may be configured to exclusively support inflation and deflation of the inflatable member 1414. In alternate embodiments, however, it is envisioned that the lumen 1412*ii* may be configured to receive one or more medical devices and/or support other functionality of the balloon catheter 1400.

The lumen 1412*iii* extends to a (second, distal) side hole 1418 that is positioned in proximity (e.g. at or adjacent) to the inflatable member 1414. For example, it is envisioned that the side hole 1418 may be positioned proximally or distally of the inflatable member 1414. Alternatively, it is envisioned that the inflatable member 1414 may overlie the side hole 1418, as seen in FIG. 18, for example, such that the side hole 1418 is in communication with the fenestration 1416 in the inflatable member 406 and the fenestration 1302 in the primary stent 1300.

In various embodiments, it is envisioned that the lumen 1412*iii* may include a "peel-away" side slit up to a rapid exchange length lumen, similar to the configuration in the Cordis Angioguard Rx. It is also envisioned that the lumen 1412*iii* may extend proximally (e.g., along the entire intravascular course of the lumen 1412*ii*) and may branch from the lumen 1412*iii* proximally (e.g., externally of the patient).

The lumen 1412*iii* is configured to receive a secondary delivery (medical) device 1600 to facilitate delivery of a secondary stent 1700 (e.g., a second fenestrated occlusion device) into a side branch S of the blood vessel V, as described in further detail below. For example, it is envisioned that the secondary delivery device 1600 may include the aforedescribed pusher 302 (FIGS. 20, 23), a secondary (second) guide wire 1800 (FIG. 22), which may be substantially similar or identical to the aforedescribed guide wire 500, or the aforedescribed balloon catheter 400 (FIG. 24). As discussed above in connection with the lumen 1412*i* and the primary guide wire 1500, it is envisioned that the lumen 1412*iii* and the medical device inserted therethrough may include corresponding (transverse) cross-sectional configurations so as to allows for relative axial movement between the medical device and the balloon catheter 1400 while inhibiting (if not entirely preventing) relative rotation between the medical device and the balloon catheter 1400.

In the context of treating a bifurcation narrowing, the primary guide wire 1500 (FIG. 18) may be introduced into a main branch M of the blood vessel V, across a limb of the narrowing (e.g., across the side branch S). The primary guide wire 1500 can then be inserted into the lumen 1412*i* in the balloon catheter 1400 such that the balloon catheter 1400 can be advanced into the blood vessel V over the primary guide wire 1500 (e.g., through the primary delivery catheter 1100) such that the inflatable member 1414 and the primary stent 1300 and, thus, the respective fenestrations 1416, 1302, are positioned in proximity (e.g., at or adjacent) to the origin of the side branch S of the blood vessel V in the manner described herein. To further facilitate control over the (rotational) orientation of the balloon catheter 1400 and, thus, the primary stent 1300, it is envisioned that the balloon catheter 1400 and the lumen 1102 of the primary delivery catheter 1100 may include corresponding non-circular (transverse) cross-sectional configurations so as to allow for relative axial movement between the balloon catheter 1400 and the delivery catheter 1100 while inhibiting (if not entirely preventing) relative rotation between the balloon catheter 1400 and the delivery catheter 1100.

Prior to expansion of the inflatable member 1414 and deployment of the primary stent 1300, the secondary stent 1700 may be inserted into the side branch S of the blood vessel V (via the second delivery device 1600), which may be either self-expanding or balloon-expandable. Alternatively, the second stent can be advanced out the side hole without the second delivery device.

In the context of a self-expanding secondary stent 1700, it is envisioned that the secondary stent 1700 may be deployed using any of the devices and methods discussed herein above. For example, it is envisioned that aforedescribed packaging catheter 300 (FIGS. 20, 23) may be utilized to deploy the secondary stent 1700. In such embodiments, the secondary stent 1700 may be supported by the pusher 302 (which extends through the elongated body 310 (FIG. 2A) of the packaging catheter 300) such that the secondary stent 1700 automatically expands upon exposure from the balloon catheter 1400. To facilitate such deployment, it is envisioned that the pusher 302 and the secondary stent 1700 may be advanced through the lumen 1412*iii* and the side hole 1418, through the fenestration 1416 in the inflatable member 1414, through the fenestration 1302 in the primary stent 1300, and into the side branch S.

It is envisioned that the pusher 302 and the secondary stent 1700 may be advanced directly through the lumen 1412*iii* in the manner illustrated in FIG. 20. Alternatively, it is envisioned that the secondary guide wire 1800 (FIG. 22) may be used, which may be substantially similar or identical to the guide wire 500 and/or the primary guide wire 1500 discussed above. In such implementations, the secondary guide wire 1800 is inserted into the side branch S through the lumen 1412*iii* prior to introduction of the pusher 302 and the secondary stent 1700. In certain embodiments, it is envisioned that the secondary guide wire 1800 may include one or more of the anchor(s) 506 (FIG. 25) discussed above in connection with the guide wire 500, which may be positioned in any suitable location.

To facilitate use with the secondary guide wire 1800, it is envisioned that the pusher 302 may include a lumen that is configured to receive the secondary guide wire 1800 (e.g., such that the pusher 302 includes a "hypotube" configuration). In such embodiments, it is envisioned that the lumen extending through the pusher 302 may include a non-circular (e.g., triangular) (transverse) cross-sectional configuration corresponding to that of the secondary guide wire 1800 to facilitate control over the relative (rotational) positions of the secondary guide wire 1800 and the pusher 302 to facilitate positioning of the secondary stent 1700 within the side branch S by inhibiting (if not entirely preventing) relative rotation between the secondary guide wire 1800 and the pusher 302 in the manner discussed above.

Figure 23:
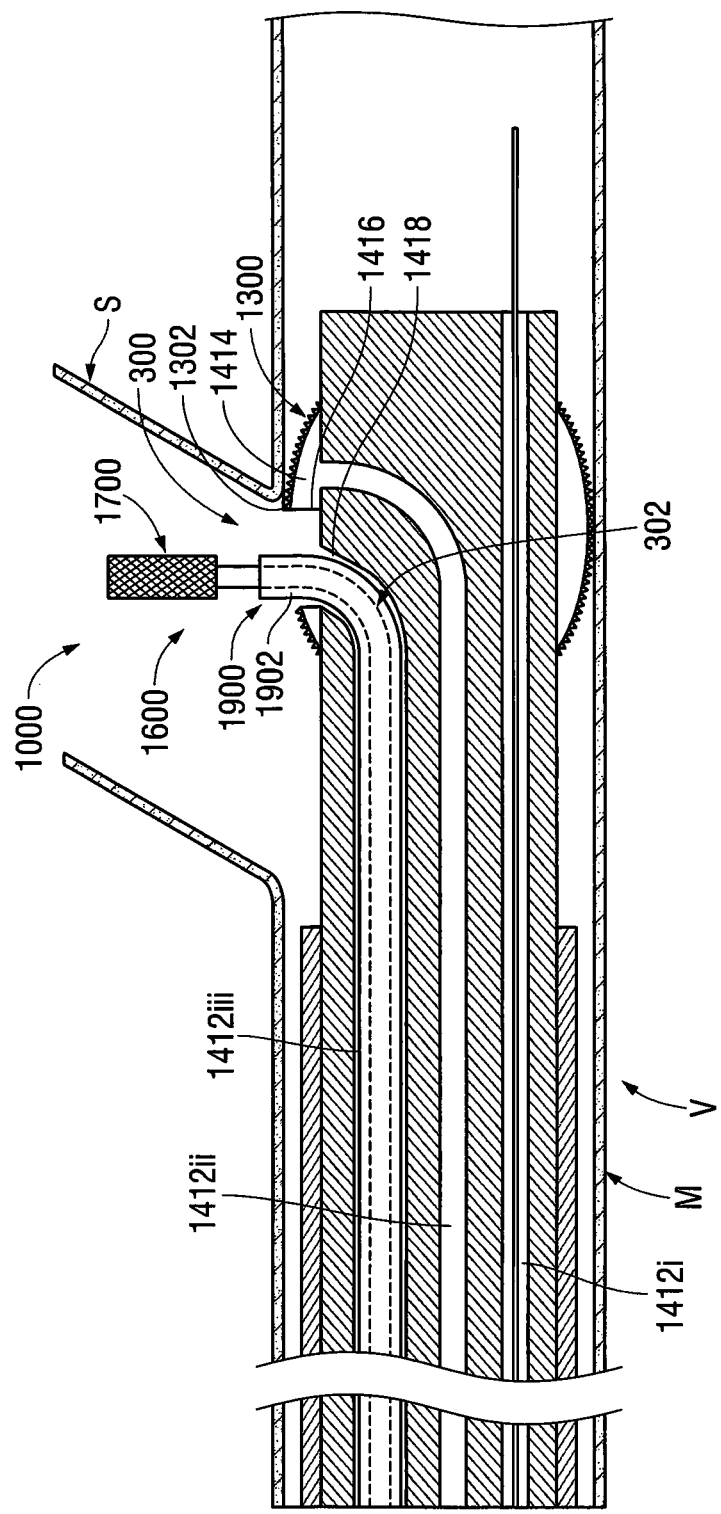
FIG. 23 is a longitudinal, cross-sectional view illustrating deployment of the self-expanding secondary stent into the side branch of the blood vessel through a secondary delivery catheter that is received within the primary delivery catheter and the first delivery device.
Figure 24:
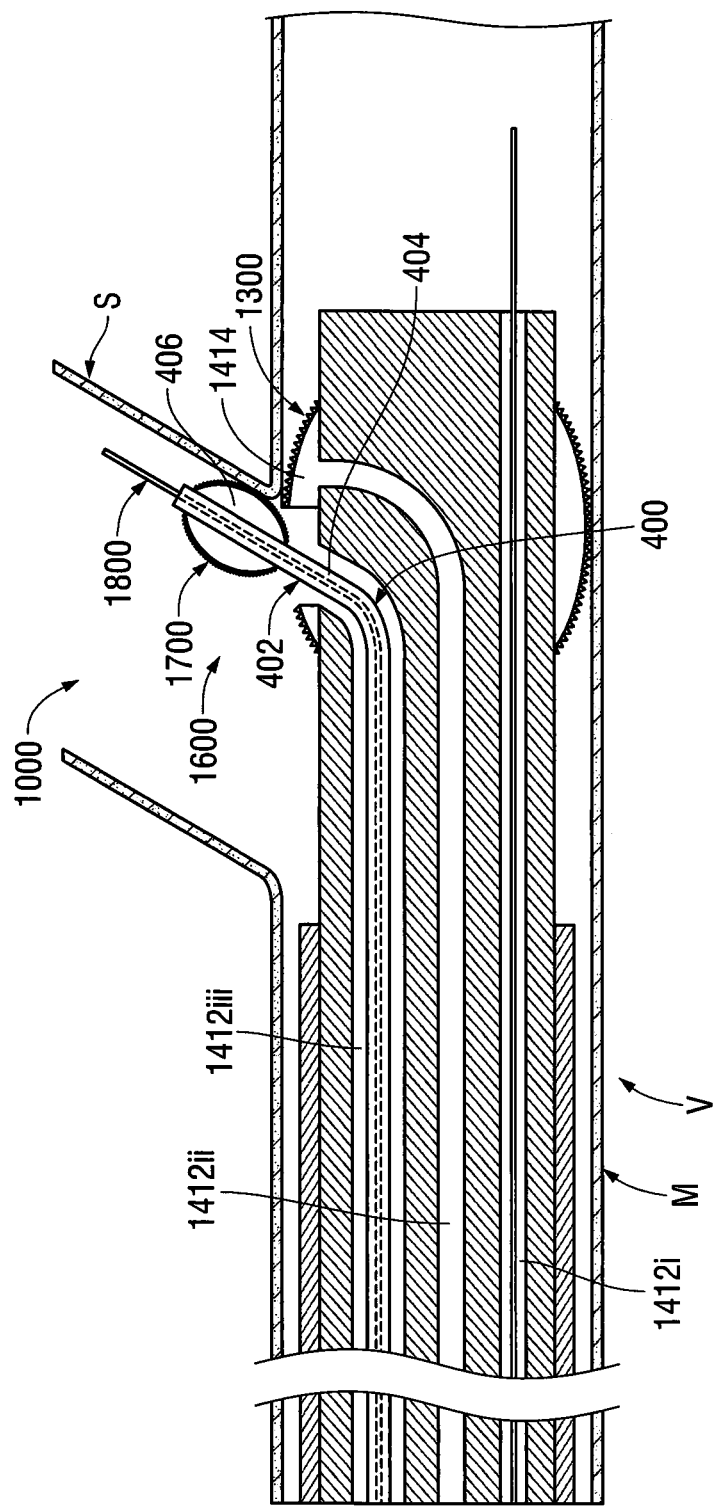
FIG. 24 is a longitudinal, cross-sectional view illustrating deployment of a balloon-expandable secondary stent into a side branch of the blood vessel through the primary delivery catheter and the first delivery device over a secondary guide wire.

Alternatively, with reference to FIG. 23, it is envisioned that a secondary delivery catheter 1900 (e.g., a hypotube) may be utilized to deploy the pusher 302 and the secondary stent 1700, which may be substantially similar or identical to the delivery catheter 100 (FIG. 1A) discussed above. In such implementations, the secondary delivery catheter 1900 includes a lumen 1902 that is configured to receive the secondary guide wire 1800 to allow for advancement of the secondary delivery catheter 1900 over the secondary guide wire 1800 and into the side branch S through the side hole 1418, through the fenestration 1416 in the inflatable member 1404, through the fenestration 1302 in the primary stent 1300, and into the side branch S. The pusher 302 and the secondary stent 1700 may then be inserted into the side branch S through the lumen 1902 of the secondary delivery catheter 1900. During such use, it is envisioned that the secondary guide wire 1800 may be removed from the secondary delivery catheter 1900 or that the secondary guide wire 1800 may remain in place in place (e.g., within the lumen 1412*iii* and within the lumen 1902 of the secondary delivery catheter 1900). For example, it is envisioned that the pusher 302 may be advanced through the lumen 1902 of the secondary delivery catheter 1900 in adjacent relation to the secondary guide wire 1800.

To facilitate control over, and proper positioning of, the secondary stent 1700 within the side branch S, it is envisioned that the lumen 1902 extending through the secondary delivery catheter 1900 and the secondary guide wire 1800 may include corresponding non-circular (e.g., triangular) (transverse) cross-sectional configurations to inhibit (if not entirely prevent) relative rotation between the secondary delivery catheter 1900 and the secondary guide wire 1800, thereby facilitating control over the (rotational) orientation of the secondary stent 1700 in the manner discussed above.

With reference to FIG. 24, in the context of a balloon-expandable secondary stent 1700, it is envisioned that the secondary stent 1700 may deployed using the aforedescribed balloon catheter 400 (FIG. 2B). During such use, following insertion of the secondary guide wire 1800 into the side branch S through the lumen 1412*iii*, the balloon catheter 400 is advanced over the secondary guide wire 1800 such that the secondary guide wire 1800 extends through the lumen 404 extending through the elongated body 402 of the balloon catheter 400. Upon sufficient advancement of the balloon catheter 400 into the side branch S over the secondary guide wire 1800, the inflatable member 406 on the balloon catheter 400, which carries the secondary stent 1700, may be expanded to thereby deploy the secondary stent 1700. To facilitate control over, and proper positioning of, the secondary stent 1700 within the side branch S, it is envisioned that the lumen 404 and the secondary guide wire 1800 may include corresponding non-circular (e.g., triangular) transverse cross-sectional configurations to inhibit (if not entirely prevent) relative rotation between the balloon catheter 400 and the secondary guide wire 1800, thereby facilitating control over the (rotational) orientation of the secondary stent 1700 in the manner discussed above. Additionally, or alternatively, it is envisioned that the lumen 1412*iii* and the elongated body 402 of the balloon catheter 400 may include corresponding non-circular (e.g., triangular) transverse cross-sectional configurations to inhibit (if not entirely prevent) relative rotation of the balloon catheter 400 within the lumen 1412*iii*. The non-circular diameter of the wire can extend along a majority of its length, starting at the proximal end positioned outside the patient's body.

In those embodiments in which the secondary stent 1700 includes fairly large interstices (e.g., so as not to significantly (substantially) impede blood flow), it is envisioned that the secondary guide wire 1800 and the corresponding medical device supporting the secondary stent 1700 (e.g., the pusher 302, the balloon catheter 400, etc.) may be devoid of the non-circular (e.g., triangular) (transverse) cross-sectional configurations discussed above. Instead, in such embodiments, it is envisioned that the secondary guide wire 1800 (and the corresponding medical device supporting the secondary stent 1700) may instead have annular (e.g., circular) transverse cross-sectional configurations to develop and deploy a "Y" configuration stent system at the bifurcation, as described in further detail below. If, however, there is a need and/or a desire to have an additional fenestration in the secondary stent 1700 overlying the origin the side branch S, then the secondary guide wire 1800 (and the corresponding medical device supporting the secondary stent 1700) may include corresponding non-circular (transverse) cross-sectional configurations to facilitate proper alignment of the fenestration in the secondary stent 1700 in the manner discussed above.

In those embodiments employing a rapid exchange configuration (e.g., such that the primary guide wire 1500 extends through a side hole in the balloon catheter 1400 and the distal end hole 1406), it is envisioned that the balloon catheter 1400 may be configured for use (deployment) in substantially straight (e.g., non-tortuous anatomy). In such methods of use, it is envisioned that the primary guide wire 1500 and the lumen 1412*i* may be devoid of the non-circular (e.g., triangular) (transverse) cross-sectional configurations discussed above. Instead, in such embodiments, it is envisioned that the primary guide wire 1500 and the lumen 1412*i* may instead have annular (e.g., circular) transverse cross-sectional configurations and that the secondary guide wire 1800 may be advanced into the side branch S via the side hole 1418 and the lumen 1412*iii*.

In the context of non-tortuous anatomical structures (of non-tortuous lengths of anatomical structures), it is envisioned that advancement of the secondary guide wire 1800 through the lumen 1412*iii*, through the side hole 1418, and into the side branch S may facilitate alignment of the secondary delivery device 1600 (e.g., the balloon catheter 400), and the components and devices inserted therethrough (e.g., the secondary stent 1700) in the intended manner (e.g., such that any included fenestration(s) in the secondary stent 1700 are positioned at the origin of the side branch S). However, in the context of most tortuous anatomical structures, it is envisioned that the employ of corresponding non-circular (e.g., triangular) (transverse) cross-sectional configurations by the secondary guide wire 1800 and the lumen 1412*iii* may facilitate proper preloading of the secondary stent 1700 in the blood vessel V in the desired orientation (e.g., such that any fenestration(s) in the secondary stent 1700 are oriented towards the origin of the side branch S).

In various embodiments, medical devices (e.g., stents, inflatable members, etc.) including multiple fenestrations are also contemplated herein (e.g., for use in the context of multiple side branches with multiple origins).

To facilitate proper location of the primary stent 1300 and/or the secondary stent 1700, it is envisioned that one or more markers (e.g., radiopaque markers) may be included to identify the proximal and distal ends thereof and/or the proximal and distal ends of any fenestration(s).

Common Method

Using any of the devices and methods above, the primary stent 1300 may be deployed such the fenestration 1302 (FIG. 17) in the primary stent 1300 is positioned in proximity (e.g., at or adjacent to) the origin of the side branch S. A guide wire (e.g., the secondary guide wire 1800) can be then advanced into the side branch S through the fenestration 1302 in the primary stent 1300 and into the side branch S to facilitate the deployment of the secondary stent 1700 using one of a variety of methods, as seen in FIGS. 20 and 22-24, for example.

Figure 25:
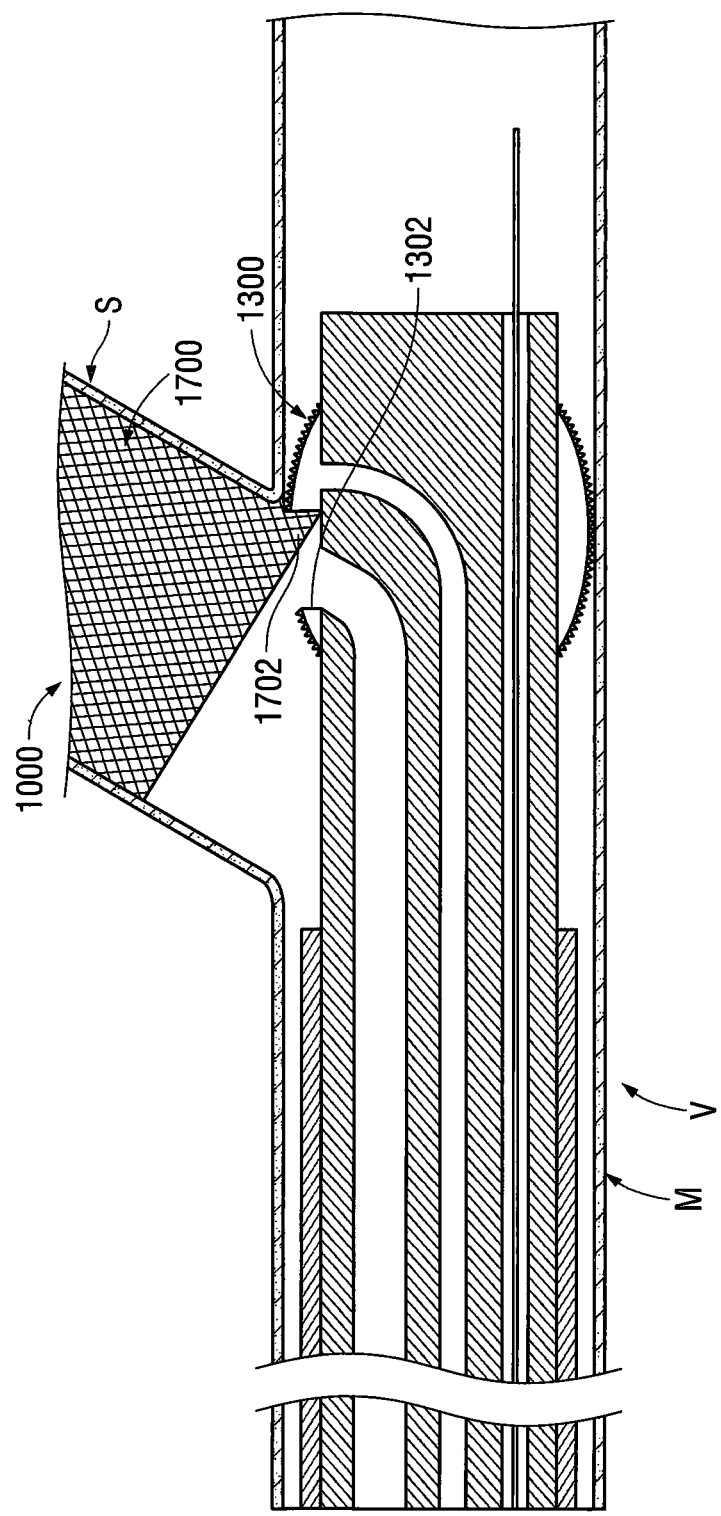
FIG. 25 is a longitudinal, cross-sectional view illustrating positioning of the secondary stent within the side branch of the blood vessel such that the secondary stent overlaps (overlies) the primary stent.

In one variation, it is envisioned that the secondary stent 1700 may be delivered over the secondary guide wire 1800 via the balloon catheter 400, as seen in FIG. 24, and positioned such that a proximal end 1702 of the secondary stent 1700 overlaps the fenestration 1302 in the primary stent 1300, as seen in FIG. 25. The devices and methods described herein facilitate precise, accurate placement of the respective primary and secondary stents 1300, 1700 to control (e.g., reduce, minimize) the extent to which the secondary stent 1700 overlaps the primary stent 1300 and thereby reduce (if not completely eliminate) leaks between the respective primary and secondary stents 1300, 1700 while avoiding unwanted obstruction of the blood vessel V by the secondary stent 1700 and accommodating for tapering in the side branch S (e.g., depending upon the particular patient's anatomy) that may result in a larger (transverse) cross-sectional dimension at the origin of the side branch S (when compared to more distal sections of the side branch S).

In a second variation, for example, it is envisioned that the secondary delivery catheter 1900 may be utilized to deploy the secondary stent 1700, as discussed above, which allows for the employ of a self-expanding configuration for the secondary stent 1700 such that the secondary stent 1700 is automatically deployed in the side branch S upon exposure of the secondary stent 1700 from the secondary delivery catheter 1900. In such procedures, it is envisioned that the secondary guide wire 1800 can be (optionally) removed. This method (and corresponding medical devices) also facilitates precise, accurate placement of the respective primary and secondary stents 1300, 1700 to control (e.g., reduce, minimize) the extent to which the secondary stent 1700 overlaps the primary stent 1300 to realize the benefits discussed above (e.g., a reduction (if not completely elimination) of leaks between the respective primary and secondary stents 1300, 1700, a reduction (if not complete elimination) of unwanted obstruction of the blood vessel V by the secondary stent 1700, and accommodation for tapering in the side branch S).

In a third variation, it is also envisioned that primary delivery catheter 1100 may be re-used instead of the secondary delivery catheter 1900.

With respect to the second and third variations, challenges regarding landing of the secondary stent 1700 may arise, especially with "woven" or "braided" stents that may be subject to foreshortening during deployment (e.g., when compared to their length during insertion and prior to deployment).

To accommodate such challenges, it is envisioned that the secondary delivery catheter 1900 may be configured in a manner similar to that discussed above in connection with the respective hypotubes 700, 800 (FIGS. 13, 14) (e.g., in correspondence with a filter-tip TAVR (transcatheter aortic valve replacement) catheter), whereby the wings 802 provide an outer constraint for the secondary stent 1700 to thereby provide control over expansion of the secondary stent 1700. To facilitate such use, as discussed above, it is envisioned that the lumen 806 extending through the inner hypotube 800 may include a non-circular (transverse) cross-sectional configurations corresponding to that of the secondary guide wire 1800 to allow for relative axial movement between the inner hypotube 800 and the secondary guide wire 1800 while inhibiting (if not entirely preventing) relative rotation between the inner hypotube 800 and the secondary guide wire 1800 to facilitate precise control over the (rotational) orientation of the secondary stent 1700. In such methods of use, the secondary stent 1700 is loaded onto the outer hypotube 700 and the inner hypotube 800 (and, thus, the wings 802) are advanced distally while the outer hypotube 700 remains (relatively) longitudinally (axially) stationary. Relative longitudinal (axial) movement between the hypotubes 700, 800 allows for exposure (and optional re-sheathing (covering)) of the secondary stent 1700. It is envisioned that enlarging the (transverse) cross-sectional dimensions of the secondary guide wire 1800 and the lumen 806 extending through the inner hypotube 800 may further reduce (if not entirely eliminate) relative rotation between the inner hypotube 800 and the secondary guide wire 1800, thereby further increasing precision in placement of the secondary stent 1700.

To offset or otherwise accommodate for any unpredictability in the expansion of "woven" or "braided" embodiments of the various stents described herein (e.g., the amount of time required to realize full expansion), it is envisioned that the proximal end of such stents (and optionally other parts as well) may include one or more rings (or other such structures) to encourage more rapid expansion and/or increase apposition between the stent and the wall of the blood vessel V. In such embodiments, it is envisioned that the ring(s) (or other structures) may include (e.g., may be formed partially or entirely from) any suitable material or combination of materials such as, for example, nitinol. It is also envisioned that (optional) longitudinal wires may connected to the stents described herein to facilitate re-sheathing when desired.

It is also envisioned that the various stents described herein may be connected to one or more external members (e.g., wires, catheters, or the like). For example, it is envisioned that that external member(s) may be connected to the proximal and distal ends of the secondary stent 1700 (which may be adapted for delivery in an "over-the-wire" or rapid exchange configuration). Following placement of the secondary guide wire 1800 in the side branch S (e.g., through the fenestration 1302 in the primary stent 1300), the secondary stent 1700 may be advanced over the secondary guide wire 1800 into the desired position and the external member(s) connected to the secondary stent 1700 may be held in place while the inner hypotube 800 (FIG. 14) (and, thus, the wings 802) is translated axially (e.g., relative to the outer hypotube 700) to exposing (un-sheath) the secondary stent 1700.

In the context of a secondary stent 1700 that is connected to one or more external members, it is envisioned that the external member(s) may expand with the secondary stent 1700. In embodiments where the secondary stent 1700 is supported by (e.g., attached to) an outer catheter or hypotube, such as the outer hypotube 700 (FIGS. 13, 14), for example, the secondary stent 1700 requires unsheathing (e.g., exposure from that the wings 802) prior to detachment (e.g., from the outer hypotube 700). However, in embodiments in which the secondary stent 1700 is devoid of such attachment, it is envisioned that the secondary stent 1700 may automatically expand and detach (proximally to distally) in a progressive manner as a result of relative longitudinal (axial) movement between the secondary stent 1700 and the wings 802.

Embodiments are also envisioned in which the secondary stent 1700 may be circumferentially attached to the outer device (e.g., the outer hypotube 700) and may include at least one additional wire attached thereto (e.g., to a distal segment of the secondary stent 1700). Additional and alternatively attachment(s) connections between the secondary stent 1700 and the outer hypotube 700 (or other such device) are also contemplated herein. For example, it is envisioned that the only a distal segment (portion) of the secondary stent 1700 may be attached (connected) to the outer hypotube 700 (or other such device). In such embodiments, it is envisioned that longitudinal (axial) advancement of the outer hypotube 700 (or other such device) may pull the attached segment of the secondary stent 1700 and push the wings 802 (and the inner hypotube 800 or other such device) in unison). Upon positioning of the secondary stent 1700 as desired, the secondary stent 1700 can be unsheathed by advancing the inner hypotube 800 (or other such device) relative to the outer hypotube 700 (or other such device) and, thus, the secondary stent 1700, to thereby un-sheath the secondary stent 1700 (from proximal to distal). If it is determined that the location of the secondary stent 1700 requires adjustment, the inner hypotube 800 (or other such device) can be moved in the opposite direction to re-sheath the secondary stent 1700 and allow for repositioning within the vasculature.

It is further envisioned that proximal attachments between the secondary stent 1700 and the outer hypotube 700 (or other such device) may be disconnected upon unsheathing of the secondary stent 1700 to facilitate appropriate orientation and position of the secondary stent 1700 (e.g., such that the secondary stent 1700 overlaps the fenestration 1302 in the primary stent 1300) without significant (substantial) overlapping of the main branch M of the blood vessel V). The secondary stent 1700 can then be detached once fully deployed.

In another embodiment, once the primary guide wire 1500 is inserted into the blood vessel v, a quaternary catheter may be utilized to help fix the (rotational) position of the primary guide wire 1500. In such embodiments, it is envisioned that the quaternary catheter may include an inner lumen with a non-circular (e.g., triangular) (transverse) cross-sectional configuration (e.g., corresponding to that defined by the primary guide wire 1500) as discussed above. It is also envisioned that the quaternary catheter may be devoid of a hub and may include a non-circular (e.g., triangular) (transverse) outer cross-sectional configuration as well as proximal and distal markers (e.g., radiopaque markers) located in any suitable position (e.g., the "12 o'clock" position) as discussed above. The primary guide wire 1500 and the quaternary catheter can be used as a guide (rail) system to facilitate delivery of the primary delivery catheter 1100 over the quaternary catheter and guidewire (e.g., to further reduce any likelihood of undesired rotation during delivery and/or deployment of the primary stent 1300).

With reference to FIGS. 1A-2A, in one particular method, the delivery catheter 100 may be utilized in connection with the pusher 302 and the stent 202 according to the following steps:

(i) insert the delivery catheter 100 into the blood vessel V;
(ii) advance the delivery catheter 100 over the guide wire 500 (FIG. 15) until the distal end 108 of the delivery catheter 100 is located in proximity (e.g., at or adjacent to) the vascular abnormality that is the subject of the procedure (e.g., the aneurysm A);
(iii) remove the guide wire 500;
(iv) orient the packaging catheter 300 (e.g., the elongated body 310, the pusher 302, and the stent 202) relative to the hub 600 to pre-set the orientation of the stent 202 relative to the aneurysm A;
(v) insert the packaging catheter 300 (e.g., the elongated body 310) into the port 602 of the hub 600;
(vi) attach the hub 600 to the proximal end 104 of the delivery catheter 100;
(vii) advance the pusher 302 (and the stent 202) from the elongated body 310 of the packaging catheter 300 into (and through) the delivery catheter 100 until the stent 202 is positioned in proximity (e.g., at or adjacent to) the aneurysm A;
(viii) partially withdraw the delivery catheter 100 while manipulating (e.g., holding or advancing) the pusher 302 to fully expose the stent 202 from the delivery catheter 100 to thereby deploy the stent 202;
(ix) withdraw the pusher 302; and
(x) withdraw the said delivery catheter 100.

Bifurcated or Y-Shaped Stents

With reference again to FIGS. 18-25, using any of the foregoing methodologies and devices, a "Y" shaped stent may be assembled (in vivo) from two stents (e.g., the primary stent 1300 and the secondary stent 1700), as seen in FIG. 25, which may be facilitated by the inclusion of a plurality of markers (e.g., radiopaque markers) on the stents 1300, 1700, the medical devices used during placement of the stents 1300, 1700, etc. For example, once the primary stent 1300 is deployed (e.g., via expansion of the inflatable member 1414), the secondary stent 1700 can be deployed in the side branch S, which may be either self-expanding or balloon-expandable. In self-expanding embodiments, seen in FIG. 23, for example, the secondary delivery catheter 1900 is advanced into the side branch S (e.g. over the secondary guide wire 1800 (FIG. 22)) through the lumen 1412*iii*, through the side hole 1418 in the balloon catheter 1400, through the fenestration 1416 in the inflatable member 1414, through the fenestration 1302 in the primary stent 1300, and into the side branch S such that the secondary stent 1700 is automatically deployed (expanded) upon exposure from the secondary delivery catheter 1900.

In certain methods, the starting point of the procedure is introduction of a non-round wire which can optionally have a stabilizer/anchor and then a device is delivered over the wire. In other methods, a device, e.g., a catheter is delivered first than the non-round wire or other device is inserted through a lumen in the catheter.

In various embodiments, it is envisioned that the secondary stent 1700 may be devoid of any fenestrations and that the secondary stent 1700 may be positioned to reduce (e.g., minimize) overlap with edges of the fenestration 1302 in the primary stent 1300. Alternatively, it is envisioned that the secondary stent 1700 can be deployed to build a "Y" shaped construct (e.g., via the methods described above used to place the primary stent 1300) to facilitate proper overlap between the stents 1300, 1700 (e.g., relative to the origin of the side branch S).

As mentioned above, it is envisioned that that the various medical devices (e.g., catheters, stents, hypotubes, guide wires, etc.) described herein may include one or more radiopaque markers (or other such components) to support external visualization. It is envisioned that such markers may be positioned in any suitable location on the corresponding medical device. For example, it is envisioned that the stents described herein may include one or more marker(s) at the proximal and/or distal ends thereof. It is also envisioned that such marker(s) may be positioned to facilitate delineation between regions of varying porosity. For example, in the context of the stent 202 seen in FIG. 2C, it is envisioned that one or more marker(s) may be positioned at the proximal and/or distal ends of the first (covered) region 204 and/or the second (uncovered) region 206. It is also envisioned that such markers may be used to delineate or define fenestration(s) such as, for example, the fenestration 1302 in the primary stent 1300.

It is envisioned that the various devices described herein may (optionally) include one or more steerable segments that are deflectable via one or more pull wires that extend within the wall of the device to facilitate insertion, removal, and/or increased precision in the placement of the device as disclosed in co-pending application Ser. No. 17/246,853, filed May 3, 2021, the entire contents of which are incorporated herein by reference. The various devices can include a plurality of segments and a plurality of pull wires connected to the segments. More specifically, the devices, e.g., the delivery catheter, can includes a plurality of inactive (passive) segments and a plurality of active (steerable, deflectable, articulable) segments that are connected to the plurality of pull wires and spaced along the longitudinal axis X. The inactive segments and the active segments can be arranged in a staggered pattern such the device alternates between inactive segments and active segments.

It is also envisioned that the various devices disclosed herein, e.g., the delivery catheter may include one or more (second) pull wires that are connected (secured, anchored) to the device to apply the selective application of a torsional (twisting) force to the device and, thus, rotational deflection of the device along all or a portion of the length thereof (e.g., at or adjacent to the distal end hole) to vary the angular position of the device as disclosed in co-pending application Ser. No. 17/246,853, the entire contents of which are incorporated herein by reference.

The markers disclosed herein for noting the circumferential rotational position that remain outside the body can be of various forms such as a dot(s), line(s) or other mark. The markers as disclosed herein that will be inside the patient's body during a procedure can be provided to be visible with imaging used to perform that procedure (e.g., radiopaque markers, visible via ultrasound and/or other imaging modalities. Alternatively they can be similar to the variations of markers used outside the body, e.g., a dot, line, etc., if direct visualization via cameras or similar technology is used. The markers as described herein can be for example on the hub, along the lumen, etc. of the elongated member, wire catheter, pusher, medical device inserted through the catheter, etc. to provide circumferential orientation.

The non-circular transverse cross sectional configurations of the outer and inner diameters of the various components herein can be of a configuration to limit or prohibit rotation. This could be in the form of corresponding configurations which are of the same or substantially the same shape or of non-circular configurations which are not necessarily the same or substantially the same but are configured so as to achieve the same objective of limiting or prohibiting rotation.

The present disclosure contemplates branched stent elements.

It is envisioned that that the various stents described herein may be fully or partially resheathable.

It is envisioned that that the various stents described herein may be detachable from the medical device supporting the stents.

It is envisioned that the various medical devices (e.g., catheters, stents, hypotubes, guide wires, etc.) and procedures described herein may be applied to various endoscopic procedures.

It is envisioned that that the various stents described herein may include any suitable (transverse) cross-sectional configuration, whether circular or non-circular (e.g., depending upon the particular procedure being performed, the patient's anatomy, the particular location of the vascular abnormality being treated, the particular nature of the vascular abnormality, etc.).

The present disclosure may also find applicability in the context of introducing other devices, such as contoured mesh sacs to cover or fill an outpouching, in a particular orientation. One of many examples of such an outpouching is a vascular aneurysm. Outpouching may also include left atrial appendage, GI outpouching, GU outpouching, heart outpouching, or any other outpouching. The implants can be temporary or permanent implants. It is envisioned that the principles of the present disclosure may support the fabrication of custom implants (e.g., to contour to the configuration of a particular lesion) and subsequent accurate placement (deployment) of such custom implants.

The various medical devices being supported by the elongate member may be non-retrievable upon deployment, retrievable upon partial deployment, and/or fully retrievable upon fully deployment. In versions where they are fully retrievable upon full deployment, or in other versions the medical device can be detachably connected to the elongate member by various mechanisms/methods such as via electrolytic, hydrostatic, mechanical, thermal etc. and can have one or more attachment sites, each with independent and/or combined detachment sites and/or mechanisms.

The various medical devices (e.g., catheters, stents, hypotubes, guide wires, etc.) and procedures described herein can also be used to deliver coated devices. Suitable examples of such coatings include (but are not limited to) lubricious compounds, sticky compounds, hydrogels, pharmaceuticals, chemotherapeutic agents, cells, proteins, etc., and combinations thereof. It is envisioned that such coatings may be located on any suitable surface of the pertinent medical device (e.g., on an inner surface, an outer surface, interstices, and combinations thereof).

The various medical devices (e.g., catheters, stents, hypotubes, guide wires, etc.) and procedures described herein may be utilized (combined) with the multiple circumferential balloon catheter previously described by Walzman (US 2020/10,543,015) to facilitate additional precision when orientating a delivery catheter in a desired (rotational) orientation within a blood vessel (e.g., at or adjacent to an aneurysm or the neck of an aneurysm).

While the medical devices and procedures described herein are generally discussed in the context of intravascular use, it should be appreciated that the medical devices and procedures described herein may find wide applicability. For example, it is envisioned that the medical devices and procedures described herein may be employed in the context of gastrointestinal and genitourinary tracts, as well as in non-biological pipes.

It will be understood by those skilled in the art that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

While the present disclosure has been described with reference to the specific embodiments thereof, it should be understood by those skilled in the art that various changes may be made (and equivalents may be substituted) without departing from the true spirit and scope of the present disclosure. In addition, many modifications may be made to adopt a particular situation, material, composition of matter, process, process step or steps, to the objective spirit and scope of the present disclosure. All such modifications are intended to be within the scope of the claims appended hereto.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure. The upper and lower limits of these smaller ranges which may independently be included in the smaller ranges is also encompassed within the present disclosure, subject to any specifically excluded limit in the stated range. Where the stated range includes one or both of the limits, ranges excluding either both of those included limits are also included in the present disclosure.

Unless defined otherwise, all technical and scientific terms used herein have the same meaning as commonly understood by one of ordinary skill in the art to which the present disclosure belongs. Although any methods and materials similar or equivalent to those described herein can also be used in the practice or testing of the present disclosure, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

Any publications discussed herein are provided solely for their disclosure prior to the filing date of the present application and each is incorporated by reference in its entirety. Nothing herein is to be construed as an admission that the present disclosure is not entitled to antedate such publication by virtue of prior disclosure. Further, the dates of publication provided may be different from the actual publication dates which may need to be independently confirmed.

Additionally, persons skilled in the art will understand that the elements and features shown or described in connection with one embodiment may be combined with those of another embodiment without departing from the scope of the present disclosure and will appreciate further features and advantages of the presently disclosed subject matter based on the description provided.

Throughout the present disclosure, terms such as "approximately," "generally," "substantially," and the like should be understood to allow for variations in any numerical range or concept with which they are associated. For example, it is intended that the use of terms such as "approximately" and "generally" should be understood to encompass variations on the order of 25% (e.g., to allow for manufacturing tolerances and/or deviations in design).

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present disclosure.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. An intravascular system for treating a blood vessel comprising:
    an elongated member defining a first lumen and a second lumen;
    a first stent having a fenestration;
    a second medical device configured for insertion into the second lumen to access a side branch of the blood vessel through a side hole and through the fenestration in the first stent;
    wherein the second medical device includes a pusher, and the second lumen of the elongated member defines a non-circular transverse cross-sectional configuration and an outer surface of the pusher defines a non-circular transverse cross-sectional configuration corresponding to the non-circular transverse cross-sectional configuration of the second lumen so as to inhibit rotation of the pusher within the second lumen to thereby control orientation of the pusher relative to the elongated member.

2. The intravascular system of claim 1, further comprising at least one circumferential marker along at least one of the lumens of the elongated member, second medical device, or pusher to mark corresponding rotational position.

3. An intravascular system for treating a blood vessel comprising:
    a first medical device including:
        an elongated member defining:
            a first lumen extending from a proximal hole to a distal hole; and
            a second lumen extending in generally parallel relation to the first lumen at least in a portion of the second lumen, the second lumen extending from near the proximal hole to a side-hole located proximally of the distal hole;
        a first inflatable member supported by the elongated member and including a first fenestration; and
        a first stent supported by the first inflatable member, the first stent configured to be deployed upon inflation of the first inflatable member, wherein the first stent includes a second fenestration; and
    a second medical device configured for insertion into the second lumen to access a side branch or a side lesion of the blood vessel through the side-hole, through the first fenestration in the first inflatable member, and through the second fenestration in the first stent; and
    wherein the second lumen defines a non-circular transverse cross-sectional configuration and an outer surface of the second medical device defines a non-circular transverse cross-sectional configuration so as to inhibit rotation of the second medical device.

4. The intravascular system of claim 3, wherein the proximal hole is at a proximal end of the elongated member for an over-the-wire configuration.

5. The intravascular system of claim 3, wherein the proximal hole is spaced from a proximalmost end of the elongated member for a rapid-exchange configuration.

6. The intravascular system of claim 3, wherein the second medical device includes:
    a body configured for connection to the first medical device and passage through the second lumen of the first medical device;
    a wire configured for passage through the second lumen through the first and second fenestrations and into the side branch or the side lesion, wherein a distal hole of the second medical device can be advanced from the second lumen, through the side-hole, first and second fenestrations, and into the side branch or the side lesion over the wire.

7. The intravascular system of claim 3, wherein the second medical device includes: a second stent supported on a pusher such that the pusher and the second stent are insertable into the side branch or the side lesion of the blood vessel through the first medical device via the second lumen and the side hole.

8. The intravascular system of claim 7, wherein the second stent is expandable in the side branch of the blood vessel.

9. The intravascular system of claim 3, wherein the non-circular transverse cross-sectional configuration of the second medical device corresponds to the non-circular transverse cross-sectional configuration of the second lumen.

10. The intravascular system of claim 3, wherein the first stent has a variable porosity along a length.

11. The intravascular system of claim 3, wherein the second medical device is a sac configured for placement in an outpouching.

12. The intravascular system of claim 3, wherein the second medical device includes a second stent configured to be deployed after the first stent has been deployed and the elongated member removed.

13. An intravascular system for treating a blood vessel comprising:
    a first medical device including:
        an elongated member defining:
            a first lumen extending from a proximal hole to a distal hole; and
            a second lumen extending in generally parallel relation to the first lumen at least in a portion of the second lumen, the second lumen extending from near the proximal hole to a side-hole located proximally of the distal hole;

a first inflatable member supported by the elongated member and including a first fenestration; and a first stent supported by the first inflatable member, the first stent configured to be deployed upon inflation of the first inflatable member, wherein the first stent includes a second fenestration; and a second medical device configured for insertion into the second lumen to access a side branch of the blood vessel through the side-hole, through the first fenestration in the first inflatable member, and through the second fenestration in the first stent;

wherein the first lumen has a noncircular shape and at least one marker corresponding to a position of the side-hole.

14. An intravascular system for treating a blood vessel comprising:
a first medical device including:
an elongated member defining:
a first lumen extending from a proximal hole to a distal hole; and
a second lumen extending in generally parallel relation to the first lumen at least in a portion of the second lumen, the second lumen extending from near the proximal hole to a side-hole located proximally of the distal hole;
a first inflatable member supported by the elongated member and including a first fenestration; and
a first stent supported by the first inflatable member, the first stent configured to be deployed upon inflation of the first inflatable member, wherein the first stent includes a second fenestration; and
a second medical device configured for insertion into the second lumen to access a side branch of the blood vessel through the side-hole, through the first fenestration in the first inflatable member, and through the second fenestration in the first stent;
wherein the second medical device is configured as a guidewire, the guidewire being insertable into the side branch of the blood vessel through the side-hole in the first medical device, the guidewire having a non-circular outer shape along at least a portion of its length, and the guidewire has at least one marker to define a circumferential position.

15. The intravascular system of claim 14, wherein the guidewire further comprises at least one segment comprising at least two wires wherein the at least two wires are configured such that when detached a detachment zone will splay and apply pressure to side walls of the vessel, and thereby help anchor the guidewire in place, and minimize longitudinal movements and rotation.

16. An intravascular system for treating a blood vessel comprising:
a first medical device including:
an elongated member defining:
a first lumen extending from a proximal hole to a distal hole; and
a second lumen extending in generally parallel relation to the first lumen at least in a portion of the second lumen, the second lumen extending from near the proximal hole to a side-hole located proximally of the distal hole;
a first inflatable member supported by the elongated member and including a first fenestration; and a first stent supported by the first inflatable member, the first stent configured to be deployed upon inflation of the first inflatable member, wherein the first stent includes a second fenestration; and
a second medical device configured for insertion into the second lumen to access a side branch of the blood vessel through the side-hole, through the first fenestration in the first inflatable member, and through the second fenestration in the first stent;
a guidewire;
wherein the second medical device is configured as a balloon catheter, the balloon catheter including:
a body;
a second inflatable member supported by the body and a second stent configured to be supported by the second inflatable member, the second stent configured to be deployed upon inflation of the second inflatable member; and
wherein the body of the balloon catheter defines a lumen configured to receive the guidewire such that the balloon catheter is insertable into the side branch of the blood vessel over the guidewire;
wherein the lumen of the balloon catheter defines a non-circular transverse cross-sectional configuration, and an outer surface of a majority of the guidewire, including a proximal end configured to be outside the patient's body, defines a non-circular transverse cross-sectional configuration to thereby inhibit rotation of the guidewire within the lumen of the balloon catheter and at least one marker on at least one of the lumen of the balloon catheter or outer surface of the guidewire to mark a particular circumferential rotational position.

17. An intravascular system for treating a blood vessel comprising:
a first medical device including:
an elongated member defining:
a first lumen extending from a proximal hole to a distal hole; and
a second lumen extending in generally parallel relation to the first lumen at least in a portion of the second lumen, the second lumen extending from near the proximal hole to a side-hole located proximally of the distal hole;
a first inflatable member supported by the elongated member and including a first fenestration; and
a first stent supported by the first inflatable member, the first stent configured to be deployed upon inflation of the first inflatable member, wherein the first stent includes a second fenestration; and
a second medical device configured for insertion into the second lumen to access a side branch of the blood vessel through the side-hole, through the first fenestration in the first inflatable member, and through the second fenestration in the first stent;
wherein an outer diameter of the second medical device is substantially similar to the second lumen of the first medical device to thereby inhibit rotation of the second medical device and a second stent and control orientation of the second stent relative to the vascular anatomy and the first medical device, and at least one rotational marker on at least one of the lumens or outer surfaces to mark a particular circumferential rotational position.

* * * * *